US012697145B2

(12) United States Patent
Leff

(10) Patent No.: US 12,697,145 B2
(45) Date of Patent: Aug. 4, 2026

(54) ZERO PROFILE SMALL STATURE PEDICLE SCREW ASSEMBLY AND ASSOCIATED METHOD OF USE

(71) Applicant: GLOBUS MEDICAL, INC., Audubon, PA (US)

(72) Inventor: David Leff, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 347 days.

(21) Appl. No.: 18/342,097

(22) Filed: Jun. 27, 2023

(65) Prior Publication Data

US 2025/0000551 A1     Jan. 2, 2025

(51) Int. Cl.
| | |
|---|---|
| *A61B 17/70* | (2006.01) |
| *A61B 17/80* | (2006.01) |
| *A61B 17/86* | (2006.01) |
| *A61B 90/00* | (2016.01) |

(52) U.S. Cl.
CPC ...... *A61B 17/7032* (2013.01); *A61B 17/7037* (2013.01); *A61B 17/7044* (2013.01); *A61B 17/7058* (2013.01); *A61B 17/809* (2013.01); *A61B 17/861* (2013.01); *A61B 90/39* (2016.02)

(58) Field of Classification Search
CPC .................................................. A61B 17/7001
See application file for complete search history.

(56) References Cited

U.S. PATENT DOCUMENTS

| | | | | |
|---|---|---|---|---|
| 7,166,109 B2 * | 1/2007 | Biedermann | ...... | A61B 17/7037 |
| | | | | 606/279 |
| 2006/0241599 A1 * | 10/2006 | Konieczynski | .... | A61B 17/7032 |
| | | | | 606/266 |

* cited by examiner

*Primary Examiner* — Andrew Yang

(57) ABSTRACT

A pedicle screw assembly that includes at least one head fixation assembly having an upper body and a lower body with an opening in a bottom portion of the lower body, at least one bone screw positioned between the upper body and the lower body of the head fixation assembly and extends outward from the opening in the bottom portion of the lower body, at least one lateral interconnecting member to stabilize at least one bone in a patient, wherein the at least one head fixation assembly is transversely attached to the at least one lateral interconnecting member; and a securing mechanism to lock the upper body to the lower body to prevent polyaxial motion and translation along the at least one interconnecting member. The interconnecting member can be at least one plate, a c-shaped member, or a walled member with slots. Navigatable screwdriver instruments can be utilized.

16 Claims, 28 Drawing Sheets

146

150

1

ZERO PROFILE SMALL STATURE PEDICLE SCREW ASSEMBLY AND ASSOCIATED METHOD OF USE

TECHNICAL FIELD

The present disclosure generally relates to a zero-profile small-stature pedicle screw assembly that decreases implant height and eliminates implant profile above the interconnecting member, e.g., rod.

BACKGROUND

Due to their age, pediatric patients typically have less tissue coverage. In addition, the height of traditional pedicle screws creates uncomfortable implant prominence where the patient may feel the implants under their skin or feel discomfort from tissue dragging over the top of the implants.

The current state-of-the-art of the pedicle screw assembly, as shown in FIG. 1, is to rest a bone screw 12 mounted polyaxially within a head fixation assembly 2 that secures a rod 3 with a top locking mechanism 4, e.g., set screw. Rod 3 functions as an interconnecting member that can stabilize at least one bone (typically several bones) after a deformity correction or after a fracture to provide protection while healing. Typically, there are a series of rods 3 connected to several head fixation assemblies 2 that are each secured to bones through bone screws 12, depending on the application.

This stack of mechanisms creates a narrow but tall implant, as shown by height 5. In small-stature systems for pediatric patients, the profile (height) is reduced by scaling both the rod and head fixation assembly. However, the profile of the head fixation assemblies remains close to the skin in some patients, with the tops of the head fixation assemblies protruding above the rod, which may cause discomfort and unwanted tissue disruption. Moreover, decreased implant size may result in decreased strength of the implant.

In addition, rod 3 must fit inside each head fixation assembly 2, restricting the ability to increase its strength and stiffness by increasing its size or varying its shape. This system reduces the system's modularity for intraoperative versatility, restricts compatibility with reduction and correction techniques, reduces the ability to create patient-specific implants tailored to patient loads and desired correction, and reduces the ability to integrate tracking features for the assessment of correction during surgery.

Thus, there exists a need in the art for a pedicle screw assembly that decreases implant height and reduces the implant profile that is currently found with this type of protruding rod-type mechanism.

SUMMARY

The following objects, features, advantages, aspects, and/or embodiments are not exhaustive and do not limit the overall disclosure. No single embodiment need provide each and every object, feature, or advantage. Any of the objects, features, advantages, aspects, and/or embodiments disclosed herein can be integrated with one another, either in full or in part.

It is a primary object, feature, and/or advantage of the present disclosure to improve on or overcome the deficiencies in the art.

It is a further object, feature, and/or advantage of the present disclosure to reorganize the mechanisms of the pedicle head fixation assembly by shifting the mechanisms from vertically stacked to horizontal. This minimizes uncomfortable tissue disruption by decreasing implant height and eliminating the profile of the implant above the rod (referred to as a zero profile). In addition, without the head fixation assembly fully restricting the rod geometry, it may be varied to increase its strength and stiffness.

It is still yet a further object, feature, and/or advantage of the present disclosure to have features that include modularity of the system for intraoperative versatility, compatibility with reduction and correction techniques, ability to create patient-specific implants tailored to patient loads, and desired correction, and the ability to integrate tracking features for the assessment of correction during surgery.

An aspect of the present invention is a pedicle screw assembly that includes at least one head fixation assembly having an upper body and a lower body with an opening in a bottom portion of the lower body, at least one bone screw positioned between the upper body and the lower body of the head fixation assembly that extends outward from the opening in the bottom portion of the lower body, at least one lateral interconnecting member to stabilize at least one bone in a patient, wherein the at least one head fixation assembly is transversely attached to the at least one lateral interconnecting member, and at least one securing mechanism to lock the upper body to the lower body to prevent polyaxial motion and translation along the at least one interconnecting member.

Another aspect of the present invention is a pedicle screw assembly where the at least one lateral interconnecting member is a lateral plate.

Yet another aspect of the present invention is a pedicle screw assembly and associated method of installation where the upper body of the head fixation assembly includes an upward extending prong that interconnects into a downward facing upper groove in a lateral plate, and the lower body of the head fixation assembly includes a downward extending prong that interconnects into an upward facing lower groove in the lateral plate.

Another feature of the present invention is a pedicle screw assembly that includes a modular clip that secures a bone screw within the lower body of a head fixation assembly.

Still another aspect of the present invention is a pedicle screw assembly that includes a securing mechanism that includes a locking bolt that connects the upper body to the lower body of the head fixation assembly.

Yet another aspect of the present invention is a pedicle screw assembly and associated method of installation having at least one interconnecting member, which includes both a first plate and a second plate positioned in parallel on each side of the head fixation assembly where the upper body of the head fixation assembly includes an upward extending prong that interconnects into a downward facing upper groove in the first lateral plate and a downward facing upper groove in the second lateral plate and the lower body of the head fixation assembly includes a downward extending prong that interconnects into an upward facing lower groove in the first lateral plate and an upwardly facing lower groove in the second lateral plate.

Still, yet another feature of the present invention is a pedicle screw assembly having a securing mechanism includes a locking screw that engages the upper body of the head fixation assembly.

Another feature of the present invention is a pedicle screw assembly and associated method of installation having at least one interconnecting member having a cylindrical opening, and the upper body of the head fixation assembly includes an upper half circle dovetail prong that interconnects into the cylindrical opening of the interconnecting member, and the lower body of the head fixation assembly includes a lower half circle dovetail prong that interconnects into the cylindrical opening of the interconnecting member and allows angulation of the interconnecting member.

Still another aspect of the present invention is a pedicle screw assembly where the interconnecting member is c-shaped.

A further feature of the present invention is the method of installing a pedicle screw assembly, where the method includes at least partially inserting the at least one bone screw into a bone of the patient with the at least one screw extender instrument, attaching a head fixation assembly to the at least one screwdriver instrument and inserting the head fixation assembly over the at least one bone screw, attaching at least one lateral interconnecting member to the head fixation assembly, further reducing the at least one bone screw into the head fixation assembly with the at least one screwdriver instrument, and connecting a securing mechanism to lock an upper body of the head fixation assembly to the lower body of the head fixation assembly to prevent polyaxial motion and translation along the at least one interconnecting member.

Yet another feature of the method of the present invention of installing a pedicle screw assembly includes at least one bone screw that includes both a first bone screw and a second bone screw, and the at least one screw extender instrument that includes both a first navigatable screw extender instrument and a second navigatable screw extender instrument, wherein each navigatable screw extender instrument utilizes a two marker array with fiducial markers aligned along a central axis of the applicable bone screw for navigated and/or robotic screw placement, wherein once the first and second bone screws have been placed, the first and second screw extender instruments continue to track the location and orientation of a patient's bone using the location and orientation of the placed first and second bone screws. Machine vision can be used as an alternative to a two marker array that may be attachable or integral to the navigable screw extender.

It is still yet another feature of the method of the present invention of installing a pedicle screw assembly that includes at least one of the first and second navigatable screw extender instruments that function as a local dynamic reference base, thereby improving navigation integrity.

It still another feature of the method of the present invention of installing a pedicle screw assembly is an orientation of the central axes of the bone screws, and the first and second navigatable screw extender instruments are recorded at an initial position with vectors defining the central axes of the navigatable screw extender instruments, which are then calculated.

It is yet another feature of the method of the present invention of installing a pedicle screw assembly is the orientation and position of the central axes of the first and second bone screws are recorded at an initial position with locations of the fiducial markers modeled by calculating their distance along the central axes of the first and second screw extenders defining an array to be tracked and recognized.

In still yet another aspect of the pedicle screw assembly of the present invention includes a plate having upwardly extending walls and at least one slot, and a plurality of bone screws, each having a pivoting washer located below the slot of the plate and a hemispherical nut located above the slot of the plate to secure the bone screw within the plate and provide angulation within a medial-lateral direction.

It is yet a further aspect of the pedicle screw assembly of the present invention is at least one slot is a plurality of slots that are each in a shape selected from the group consisting of a circle, a square, an oval, and a rectangle.

Still, yet another feature of the pedicle screw assembly of the present invention includes a plurality of slots that are interconnected by members, wherein the members have a cross-section that is selected from the group consisting of a circle, a square, an I-beam, and a rectangle structured to accommodate a patient's anatomy and corresponding medical treatment requirements. The structural portions of the plate bridge the slots such that they have sufficient strength and stiffness for correction and physiological loading, do not interfere with bony anatomy, and minimize the profile of the implant. The structural portions can be created through generative modeling to optimize stiffness. The generative model utilizes a number of inputs, including design, cost, dimensions, and patient scans. Other variables are inputted, including material performance parameters, design rules, design process constraints, and construction constraints, whereby the output is generated and transformed into CAD drawings and CAM data for 3D printing or other automated manufacturing processes.

Referring now to FIG. 31, the flowchart for the generative model creation of a plate bridge is generally indicated by the numeral 300. Process steps are indicated by <nnn> as indicated below. The first step is to obtain the fundamental requirements <302>. This can include, but is not limited to, patient scan data, potential plate designs, potential plate dimensions, costs, and physical information on plate material and holes. This information is provided as inputs <304>. These inputs <304> are combined with rules and constraints <306>, including, but not limited to, plate structure constraints, hole structure constraints, human anatomy constraints, plate and hole construction constraints, design process and rules, and so forth. The combination of rules and constraints <306> and inputs <304> are combined in the generative model <308> that creates an optimal plate to address the patient's condition in view of effectiveness, safety, and cost. This the then generated as an output <310>. This output is then transformed into a CAD/CAM model for preferably, but not necessarily, an automated manufacturing process <312>.

These and/or other objects, features, advantages, aspects, and/or embodiments will become apparent to those skilled in the art after reviewing the following brief and detailed descriptions of the drawings. The present disclosure encompasses (a) combinations of disclosed aspects and/or embodiments and/or (b) reasonable modifications not shown or described.

BRIEF DESCRIPTION OF THE DRAWINGS

Several embodiments in which the present disclosure can be practiced are illustrated and described in detail, wherein like reference characters represent like components throughout the several views. The drawings are presented for exemplary purposes and may not be to scale unless otherwise indicated.

An artisan of ordinary skill in the art need not view, within isolated figure(s), the near-infinite distinct combinations of features described in the following detailed description to facilitate an understanding of the present disclosure.

DETAILED DESCRIPTION

The present disclosure is not to be limited to that described herein. Mechanical, electrical, chemical, procedural, and/or other changes can be made without departing from the spirit and scope of the present disclosure. Unless otherwise indicated, no features shown or described are essential to permit basic operation of the present disclosure.

Figure 2:
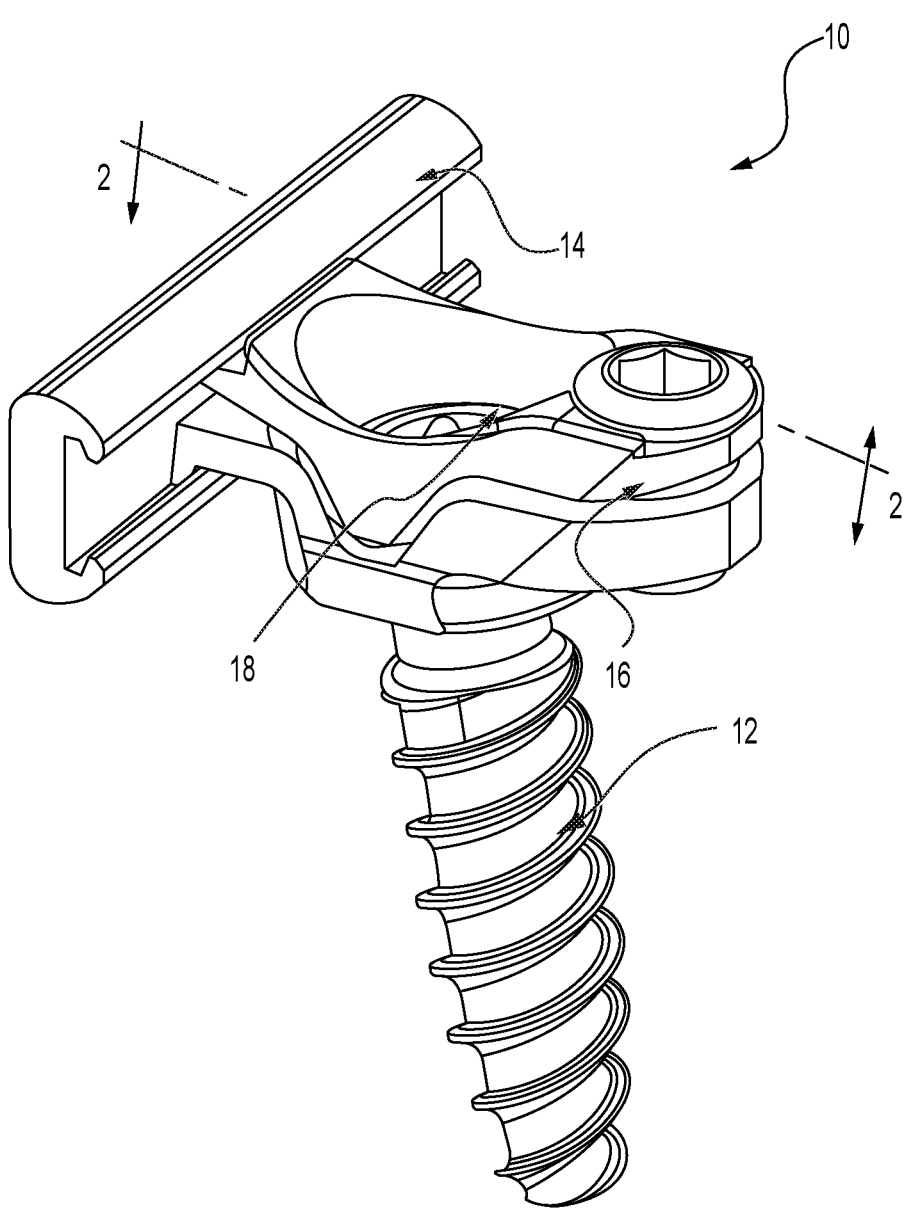
FIG. 2 is a perspective view of a first embodiment of a head fixation assembly that receives a bone screw, where the head fixation assembly is attachable to a lateral plate.

Referring now to FIG. 2, a pedicle screw assembly of the present invention is generally indicated by the numeral 10. The pedicle screw assembly 10 includes a bone screw 12 having a top 18 that is secured within a head fixation assembly 16. The head fixation assembly 16 is laterally attached to an interconnecting member that is preferably, but not necessarily, a lateral plate 14. A lateral plate 14 performs a comparable function to that of a rod, which is an interconnecting member that can stabilize at least one bone (and typically several bones) after surgical intervention to provide protection to the patient while healing. Typically, there are a series of lateral plates 14 connected to several head fixation assemblies 16 that are each secured to bones through bone screws 12 depending on the application, which include the extent of the fractures or the extent of the deformity correction.

Figure 3:
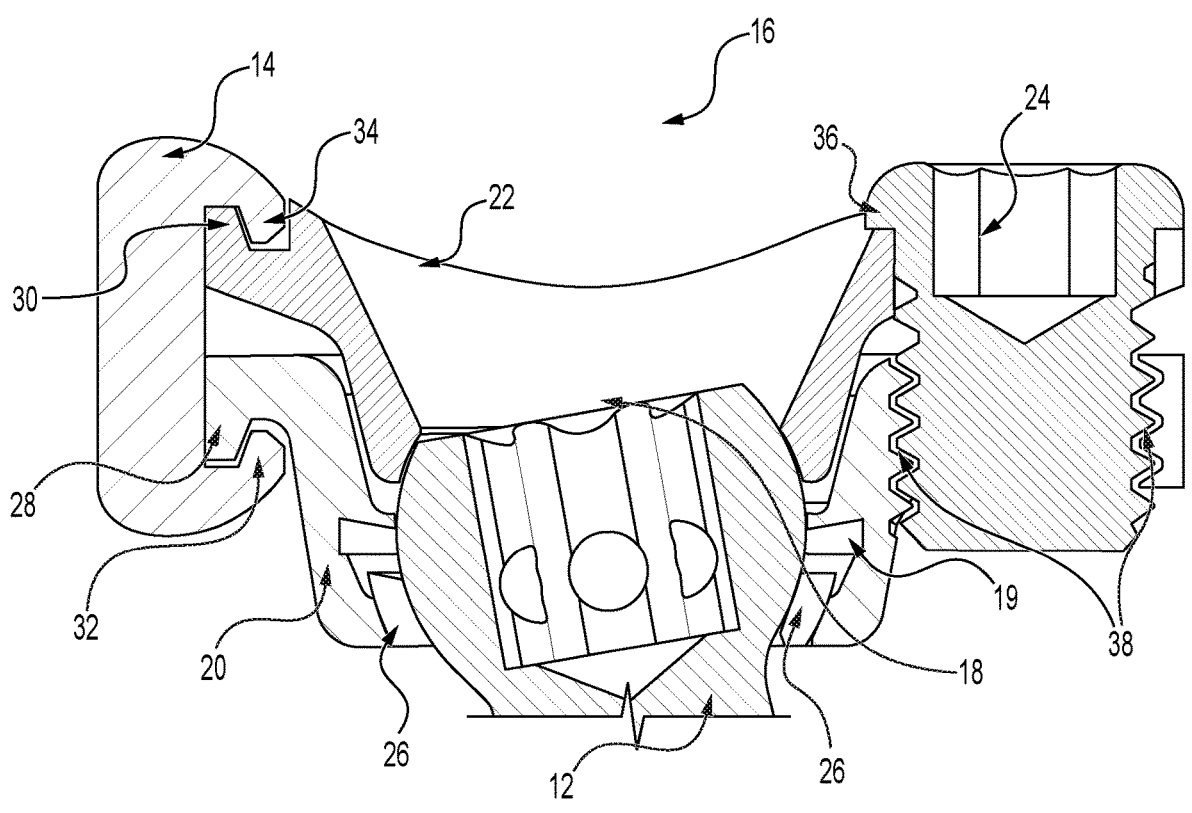
FIG. 3 is a sectional view along line 2-2 in FIG. 2 of the head fixation assembly that receives a bone screw where the head fixation assembly is attachable to a lateral plate.

Referring now to FIG. 3, the head fixation assembly 16 is shown in greater detail, which includes a lower body 20 and an upper body 22 that holds the top 18 of the bone screw 12 in a fixed position. Preferably, but not necessarily, there is a modular clip 26 that secures the top 18 of the bone screw 12 inside the lower body 20. The modular clip 26 has a spherically tapered outer surface that interacts with a recess 19 with two radiused tapers so that the modular 26 can angle or tilt with the bone screw 12.

The lower body 20 includes a downward extending prong 28 that interconnects into an upward-facing lower groove 32 of the lateral plate 14. The upper body 22 includes an upward-extending prong 30 that interconnects into a downward-facing upper groove 34 of the lateral plate 14. This forms a dovetail type of configuration.

There is a myriad of mechanisms that can secure the upper body 22 to the lower body 20 on the side opposite the lateral plate 14. Preferably, a locking bolt 24 can be utilized that includes an upper flange 36 that secures the top portion of the upper body 22. The lower body 20 of the head fixation assembly 16 is held into position with the locking bolt 24 through a threaded opening 38.

Once sufficient correction has been achieved, the polyaxial motion and translation along the lateral plate 14 are locked by tightening the locking bolt 24. The locking bolt 24 pivots the upper body 22 towards the lower body 20 about the top of the bone screw 18 until the downward extending prong 28 and the upward extending prong 30 compresses against the upward facing lower groove 32 and the downward facing upper groove 34, respectively, of the lateral plate 14. Continued tightening creates compression on the top of the bone screw 18 and compression on the lateral plate 14, locking it rotation and translation, respectively.

Figure 1:
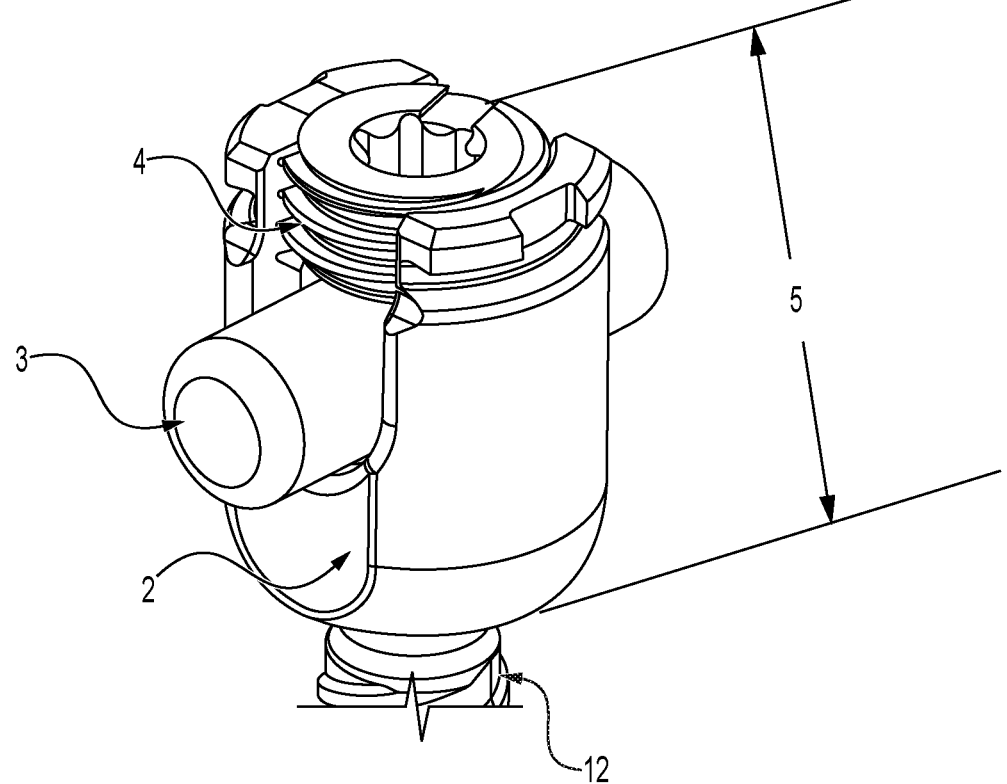
FIG. 1 shows a perspective view of a typical prior art bone fastener assembly, including a bone screw positioned in a head fixation assembly below a rod that is secured with a top locking mechanism, e.g., a set screw.
Figure 4:
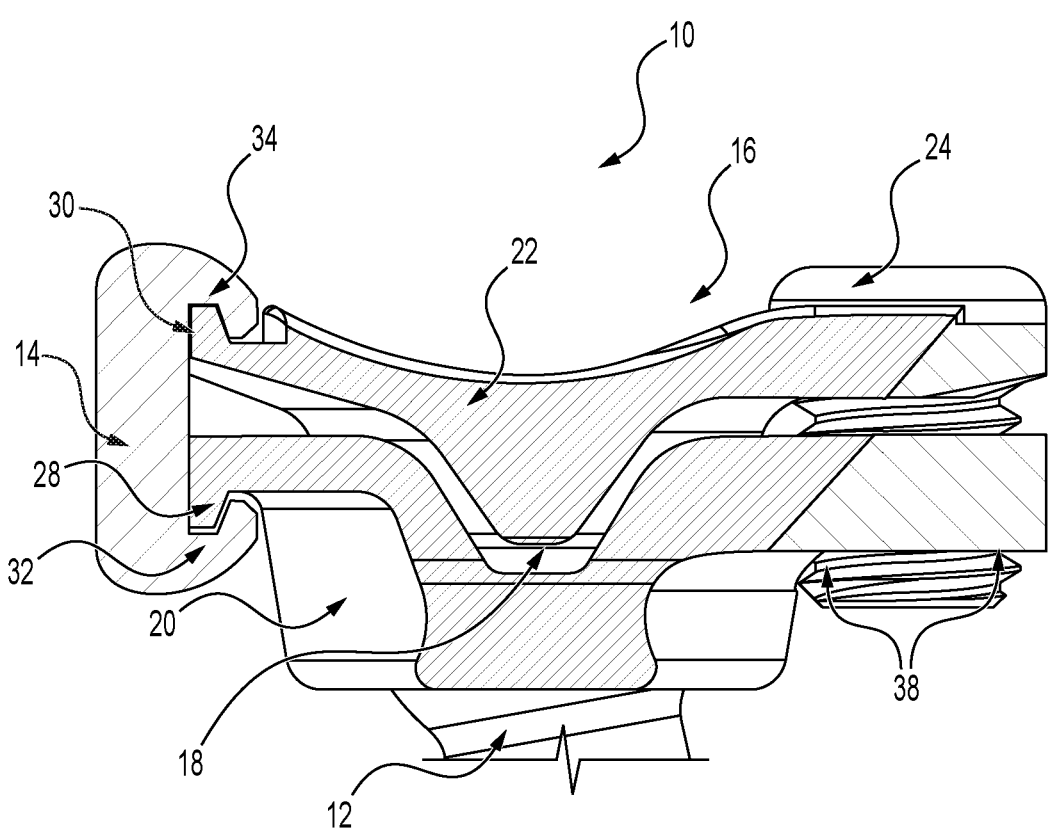
FIG. 4 is a front view of the first embodiment of a head fixation assembly that receives a bone screw, where the head fixation assembly is attachable to a lateral plate where the lateral plate has an increased height.

Referring now to FIG. 4, the lateral plate 14 can be longer to provide significantly greater height for the pedicle screw assembly 10 since the lateral plate 14 is not restricted in geometry like the position of the prior art circular rod 3 shown in FIG. 1 for a prior art head fixation assembly 2. Therefore, the height of the lateral plate 14 may be increased compared to the position of the prior art circular rod 3 without drastically increasing the profile of the entire implant. In addition, this increased height allows for increased stiffness in the sagittal plane. In addition, the width of the lateral plate 14 can be increased to increase stiffness in the coronal and axial planes, thereby potentially improving treatment effectiveness.

Figure 5:
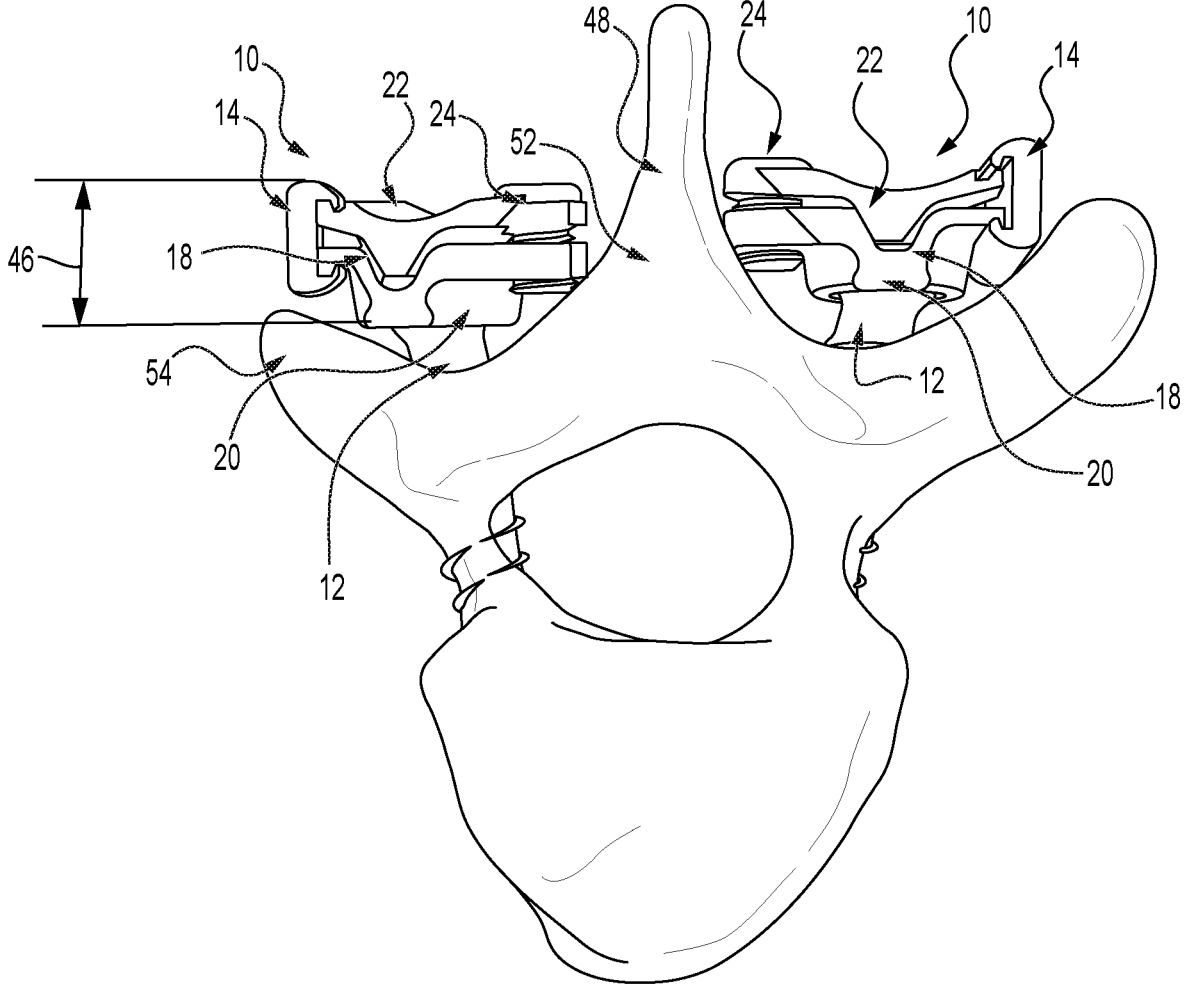
FIG. 5 is a front view of dual first embodiments of a head fixation assembly that receives a bone screw, where the head fixation assembly is attachable to a lateral plate having an increased height that is attached to a thoracic vertebra.

Referring now to FIG. 5, the advantage of the design of the pedicle screw assembly 10 having the lateral plate 14 and the locking bolt 24 is to have a vertical offset 46 from the top of the screw 18 is that the implant 48 can seat closer to the lamina 52 and transverse process 54. Therefore, the overall height of the pedicle screw assembly 10 is decreased compared to the prior pedicle screw systems.

Figure 6:
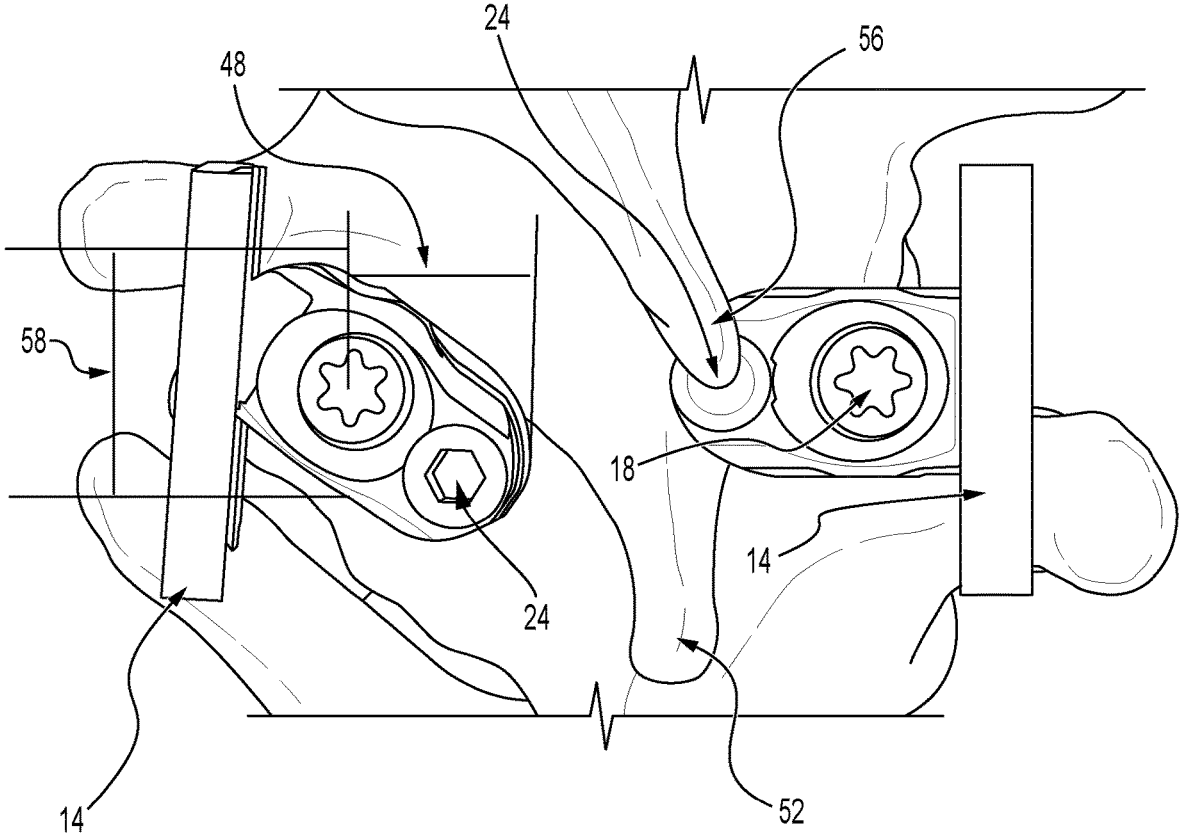
FIG. 6 is a top view of the dual first embodiments from FIG. 5 of a head fixation assembly that receives a bone screw, where the head fixation assembly is attachable to a lateral plate having an increased height that is attached to a thoracic vertebra with both angled and straight bone head fixation assemblies.

Referring now to FIGS. 5 and 6, the upper bodies 20 and lower bodies 22 may be angled or perpendicular to the lateral plate 14. An angle decreases the distance to the medial side of the implant 48 to avoid the spinous process 56. A spinous process 56 is bony projections that arise at right angles (perpendicular) to the midline of the lamina 52. However, the depth of implant 44 is increased, i.e., run-on-rod 58.

Figure 7:
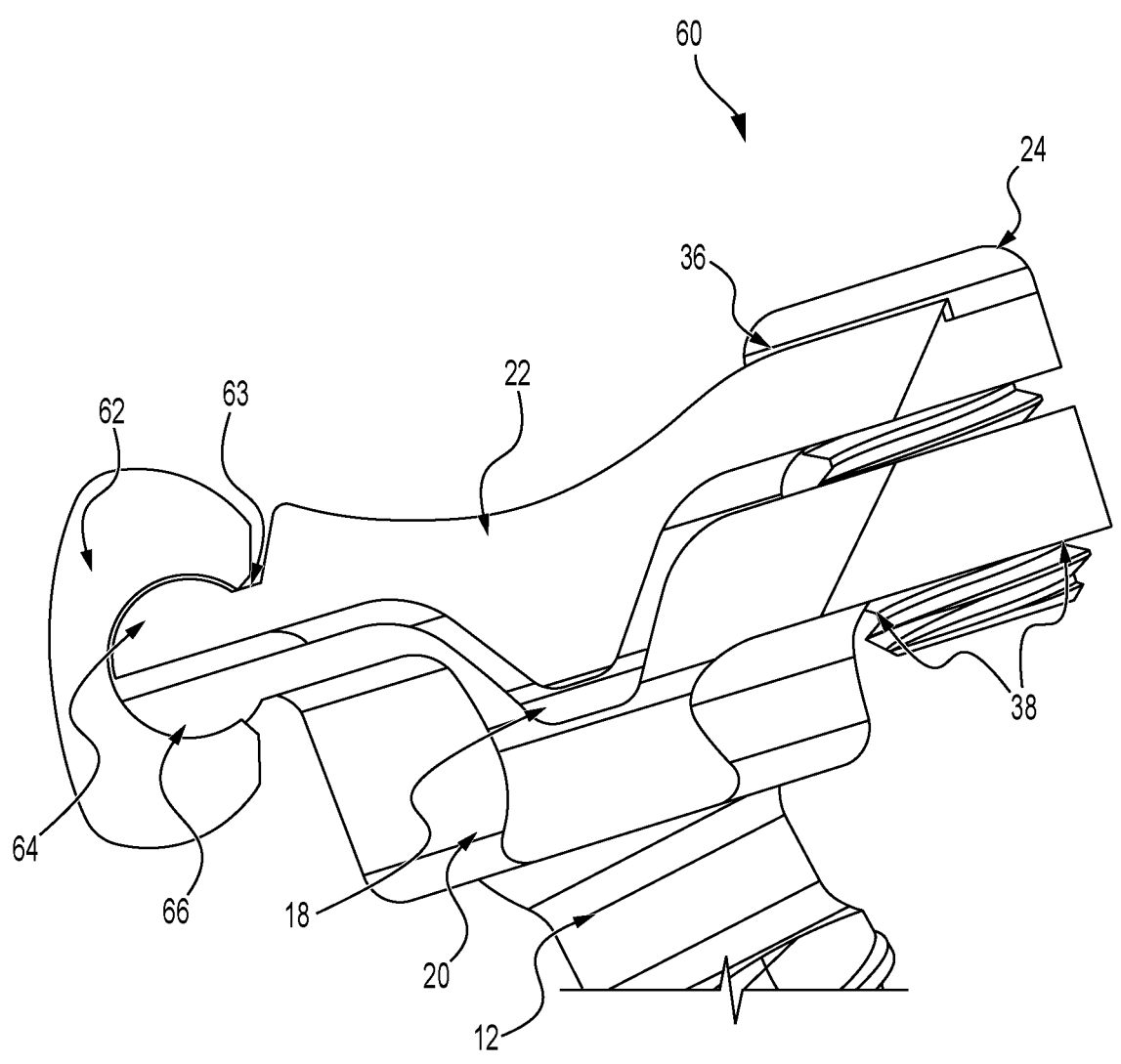
FIG. 7 is a front view of a second embodiment of a head fixation assembly that receives a bone screw with an interconnecting member having a cylindrical opening, and the upper body of the head fixation assembly includes an upper half circle dovetail prong that interconnects into the cylindrical opening of the interconnecting member, and the lower body of the head fixation assembly includes a lower half circle dovetail prong that interconnects into the cylindrical opening of the interconnecting member and allows angulation of the interconnecting member.

A second embodiment of the first embodiment shown in FIG. 2 is that shown by the numeral 60 in FIG. 7. The difference is focused on where the interconnecting member 62 can be a wide variety of shapes, including that of a c-shaped curved structure as shown with a cylindrical opening 63. In this case, the lower body 20 includes a lower half circle dovetail prong 66 that interconnects within the lower portion of the cylindrical opening 63 of the interconnecting member 62. In addition, the upper body 22 includes an upper half circle dovetail prong 64 that interconnects within the upper portion of the cylindrical opening 63 of the interconnecting member 62. In addition, this allows angulation about the interconnecting member 62 so that the top of the bone screw 18 does not need to be perpendicular to an opening formed by the upward-facing lower groove 32 and downward upper groove 34 in the lateral plate 14, as shown in FIG. 3.

Figure 8:
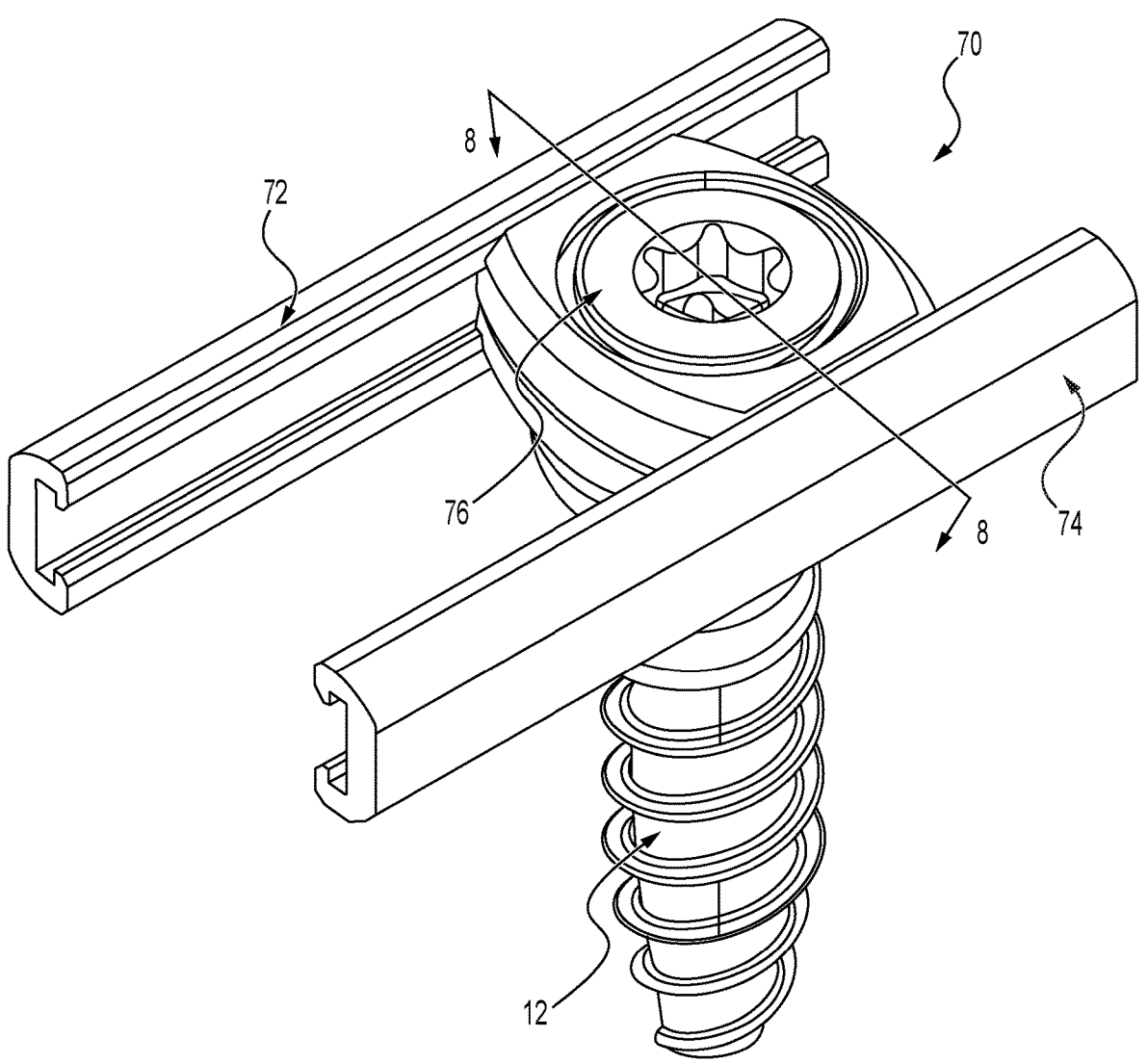
FIG. 8 is a perspective view of a third embodiment of a head fixation assembly that receives a bone screw, where the head fixation assembly is attachable on both sides to two symmetrical lateral plates.
Figure 9:
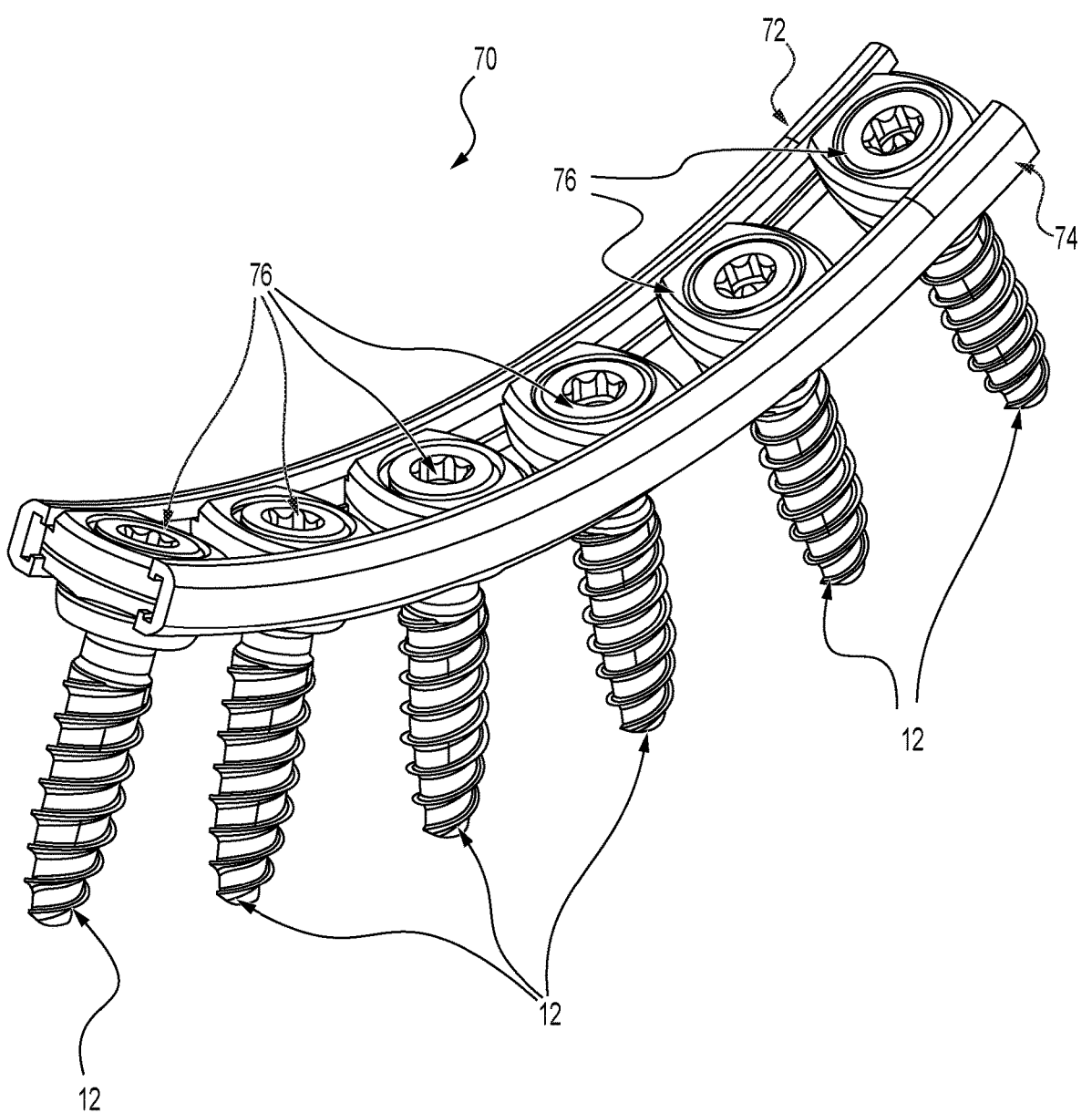
FIG. 9 is a perspective view of the third embodiment of a series of head fixation assemblies that each receives a bone screw, where each of the head fixation assemblies is attachable on both sides to two symmetrical lateral plates.

A third embodiment is indicated by the numeral 70 in FIGS. 8 and 9. This concept is similar to the pedicle screw assembly 10 in FIG. 2 with the exception that there is now a symmetrical structure with interlocking members, including both a first lateral plate 72 and a second lateral plate 74 rather than a single lateral plate 14 on one side and a locking bolt 24 on the other side. As shown in FIG. 9, there are a series of bone screws 12 held in a series of head fixation assemblies 76. The series of head fixation assemblies 76 are held in position by the previously referenced first lateral plate 72 and a second lateral plate 74 on each side. It is also believed that the second embodiment of FIG. 7 can also be structured to be placed in dual symmetrical interconnecting members 62 surrounding a head fixation assembly in accordance with the design of this third embodiment.

Figure 10:
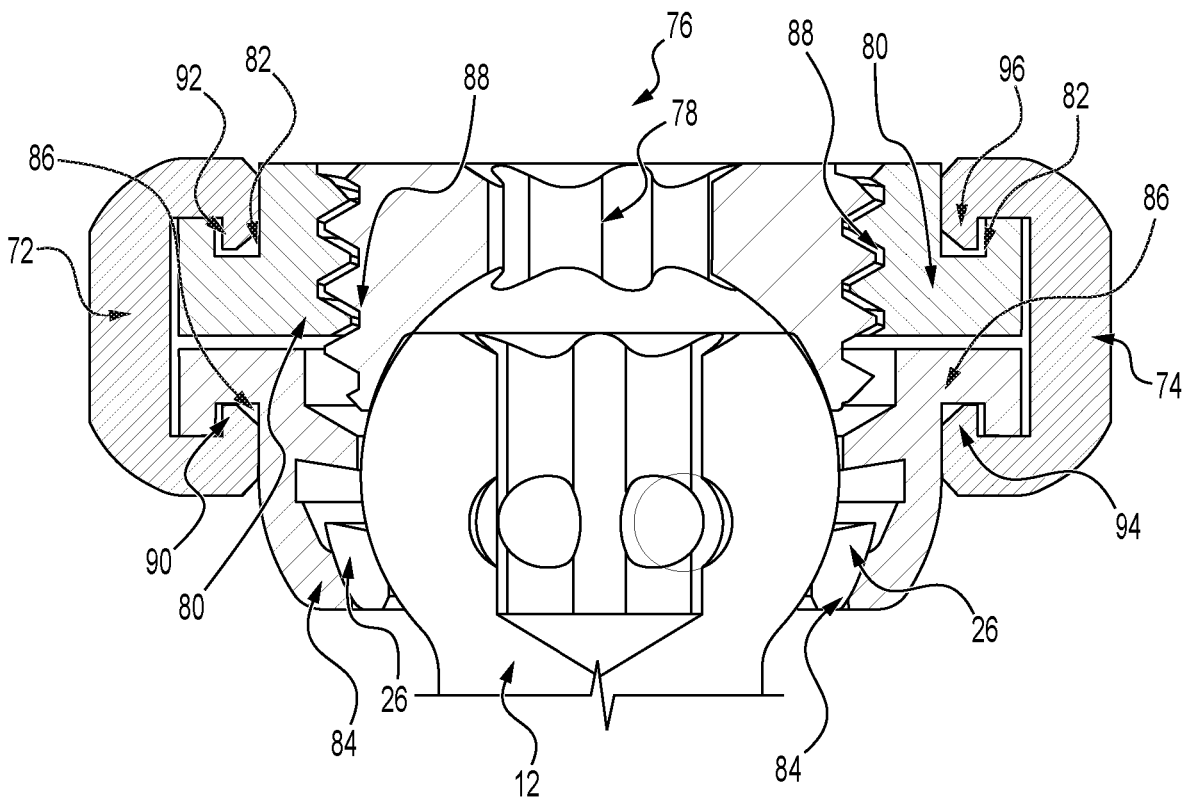
FIG. 10 is a sectional view along line 8-8 in FIG. 8 of the third embodiment of a head fixation assembly that receives a bone screw, where the head fixation assembly is attachable on both sides to two symmetrical lateral plates.

Referring now to FIG. 10, a detailed view of the head fixation assembly 76 is shown. This includes an upper member 80 and a lower member 84 that are connected together through a center locking screw 78 inserted and tightened in a threaded opening 88 to lock the angulation of the bone screw 12 and translation along a first lateral plate 72 and a second lateral plate 74. As before, there is a modular clip 26 that is preferred for securing the bone screw 12 within the lower member 84.

The first lateral plate 72 is secured to the upper member 80 through a downward extending prong 92 of the first lateral plate 72 that engages an upward facing upper groove 82 of the upper member 80 and the first lateral plate 72 is secured to the lower member 84 through an upward-facing lower prong 90 of the first lateral plate 72 that engages a downward-facing lower groove 86 in the lower member 84.

The second lateral plate 74 is secured to the upper member 80 through a downward extending prong 96 of the second lateral plate 74 that engages an upward facing upper groove 82 of the upper member 80 and the second lateral plate 74 is secured to the lower member 84 through an upward facing lower prong 94 of the second lateral plate 74 that engages a downward facing lower groove 86 in the lower member 84. This provides a solid structure with two lateral plates providing interconnecting members.

Figure 11:
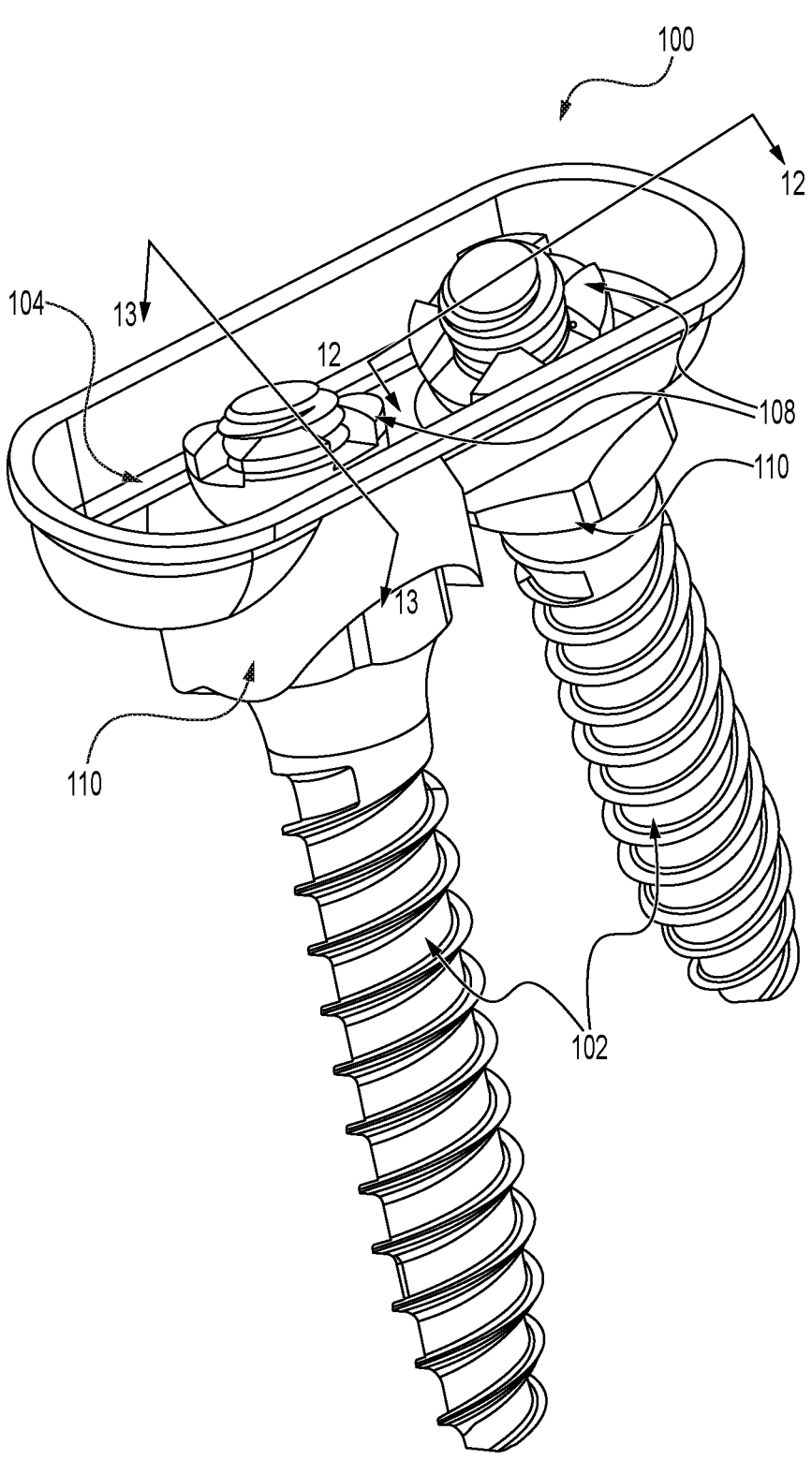
FIG. 11 is a perspective view of a fourth embodiment of a patient-specific plate where dual bone screws are inserted therein and tightened by hemispherical nuts with pivoting washers for angulation.

A fourth embodiment is indicated by the numeral 100 in FIG. 11. This includes at least one bone screw 102 inserted into a plate 104 with preferably, but not necessarily, curved sidewalls. The bone screws 102 are tightened into plate 104 by hemispherical nuts 108. Pivoting washers 110 may be used to allow angulation of the bone screws 102 in the medial-lateral direction.

Figure 12:
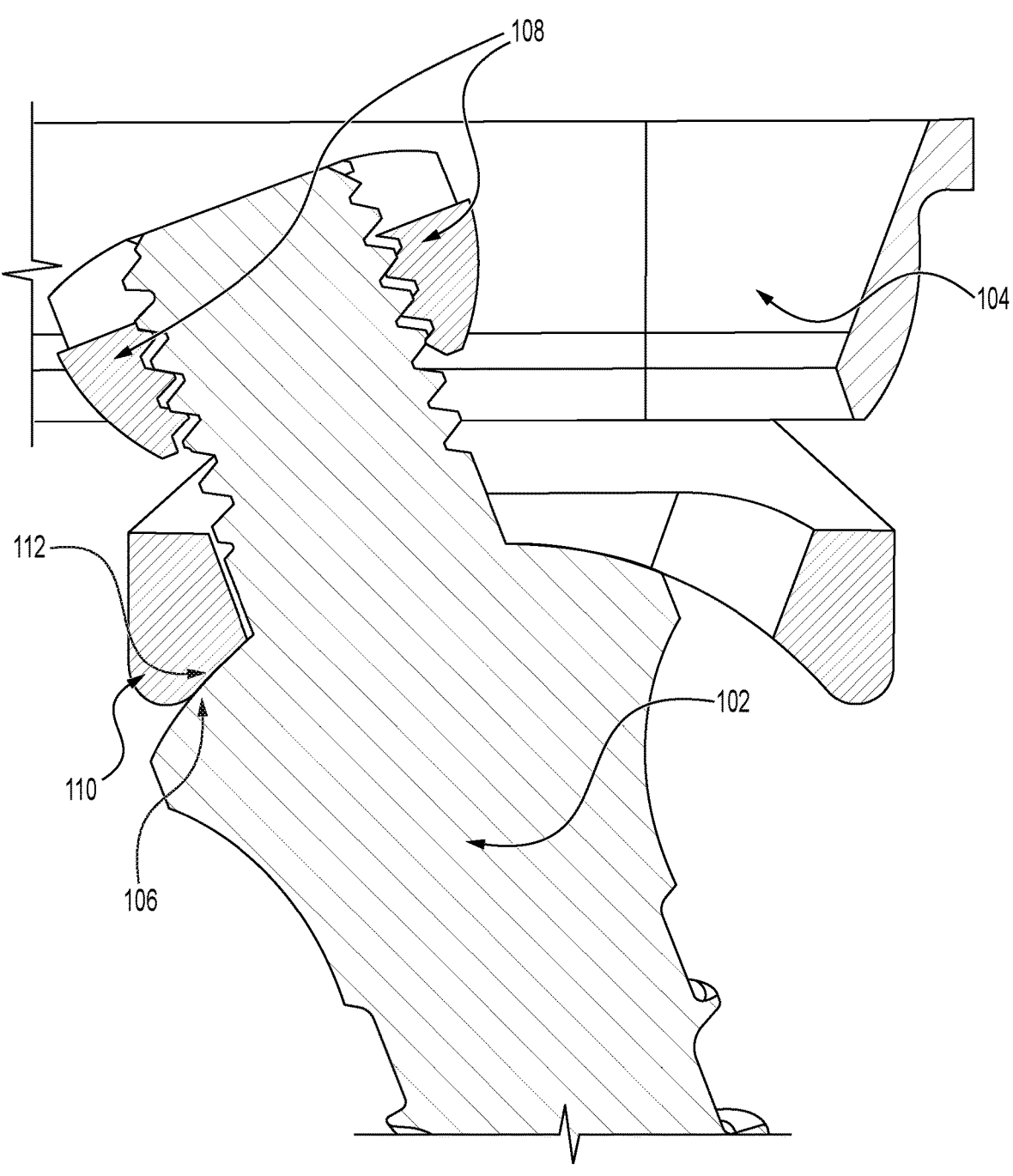
FIG. 12 is a sectional view along line 12-12 in FIG. 11 of the fourth embodiment of a patient-specific plate where dual bone screws are inserted therein and tightened by a hemispherical nut with a pivoting washer for angulation.
Figure 13:
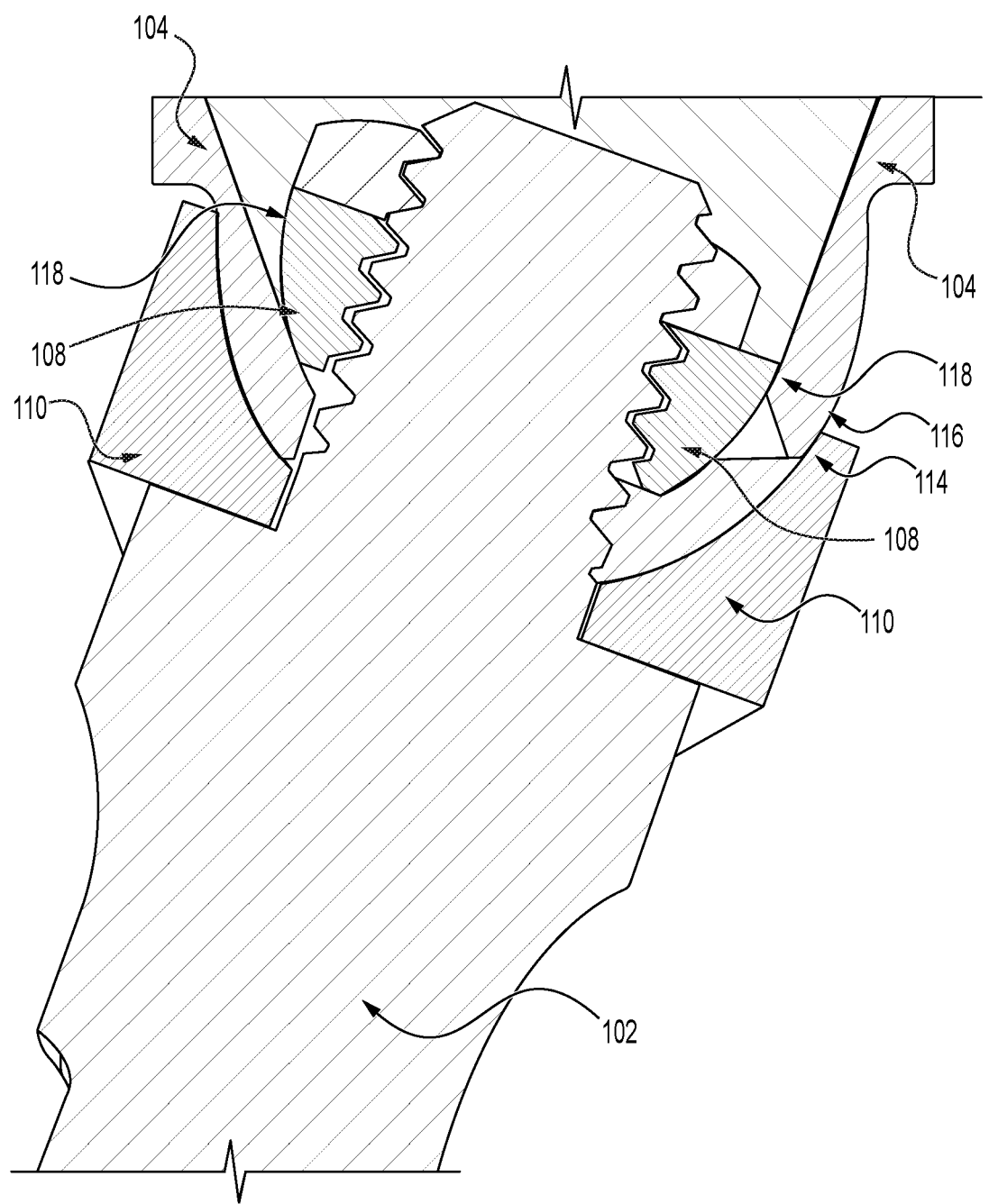
FIG. 13 is a sectional view along line 13-13 in FIG. 11 of the fourth embodiment of a patient-specific plate where dual bone screws are inserted therein and tightened by a hemispherical nut with a pivoting washer for angulation.

Referring now to FIG. 12, bone screw 102 includes a curved surface 106 that allows for angulation in the cephalad-caudal direction. The pivoting washer 110 has a mating cephalad-caudal curved surface 112, Referring now to FIG. 13, the pivoting washer 110 also has a medial-lateral curved surface 114 that angles against the exterior curved surface 116 of the plate 104. The hemispherical surface 118 of the hemispherical nut 108 contacts the inside slot 118 of the plate 104 to lock the connection and permit angulation. The tightening of the hemispherical nut 108 compresses the joint and locks the angulation.

Figure 14:
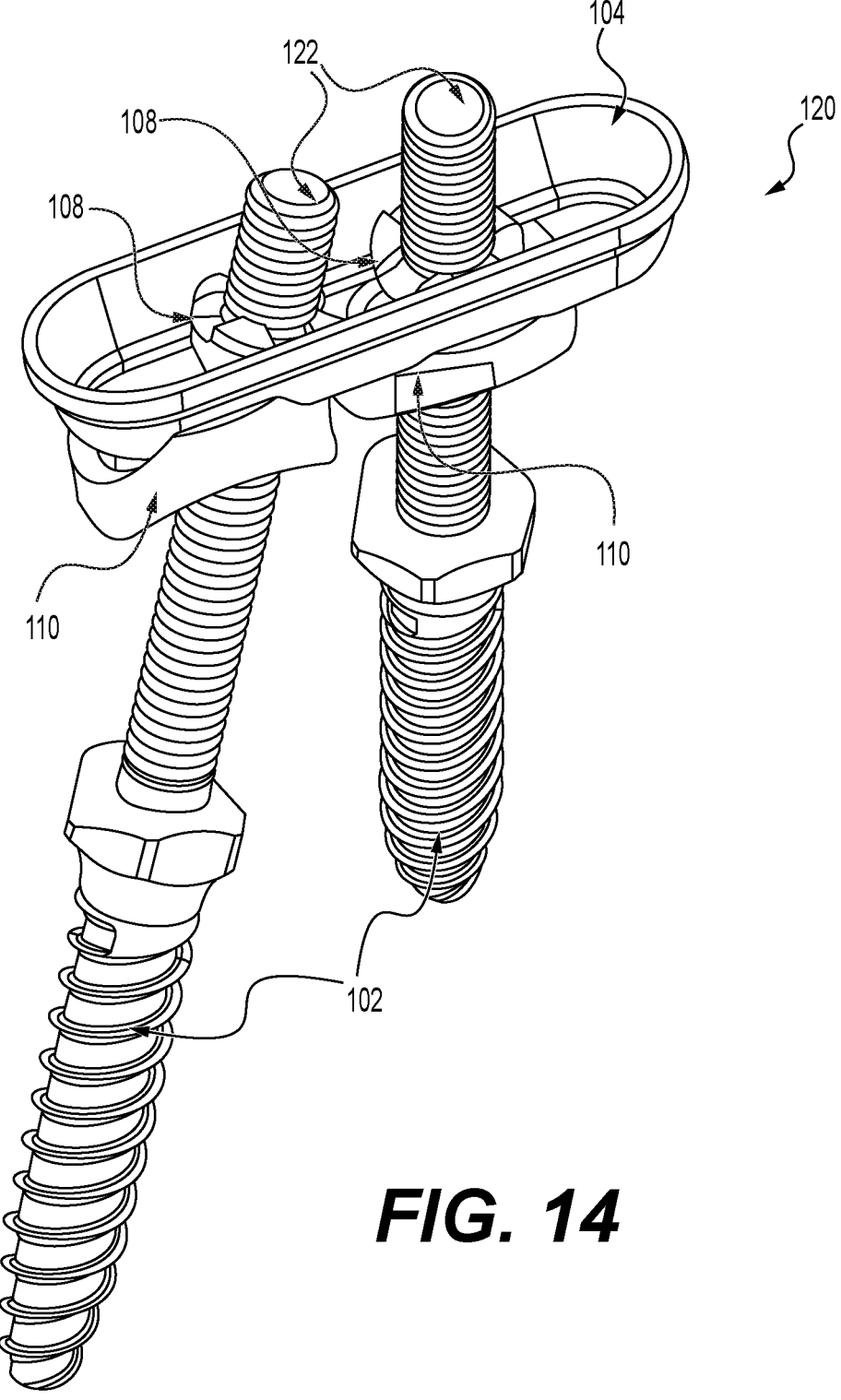
FIG. 14 is a perspective view of the fourth embodiment of a patient-specific plate where extended reduction posts are shown.

Referring now to FIG. 14, which is comparable to FIG. 11, is a fifth embodiment 120 that has bone screws 102 with extended reduction posts 122. Extended reduction posts 122 may be used to reduce the bone screws 102 to plate 104 by threading the hemispherical nuts 108. In addition, the extended reduction posts 122 may be used for tracking correction on the spine, similar to the use of screw extenders described in detail below. The posts are then removed after reduction with a pin cutter (not shown).

Figure 15:
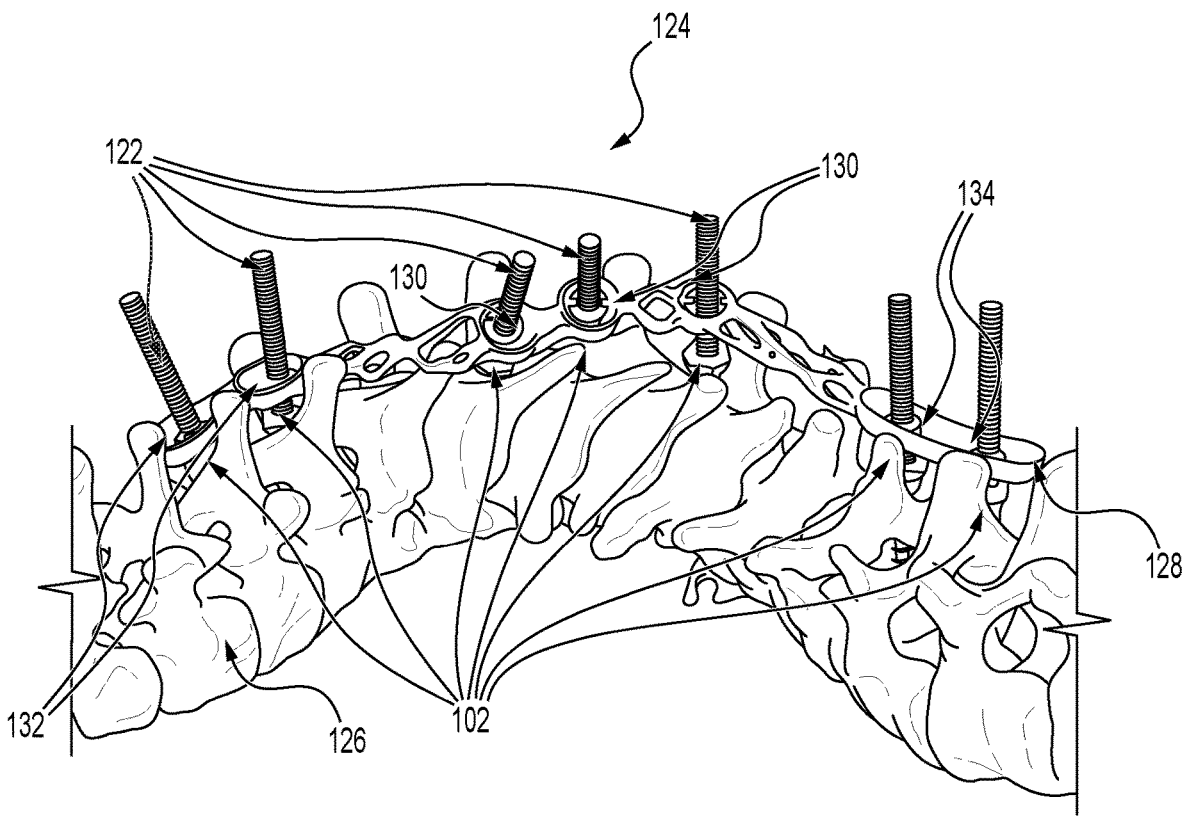
FIG. 15 is a perspective view of the fourth embodiment of a patient-specific plate bridge applied to a human spine.
Figure 16:
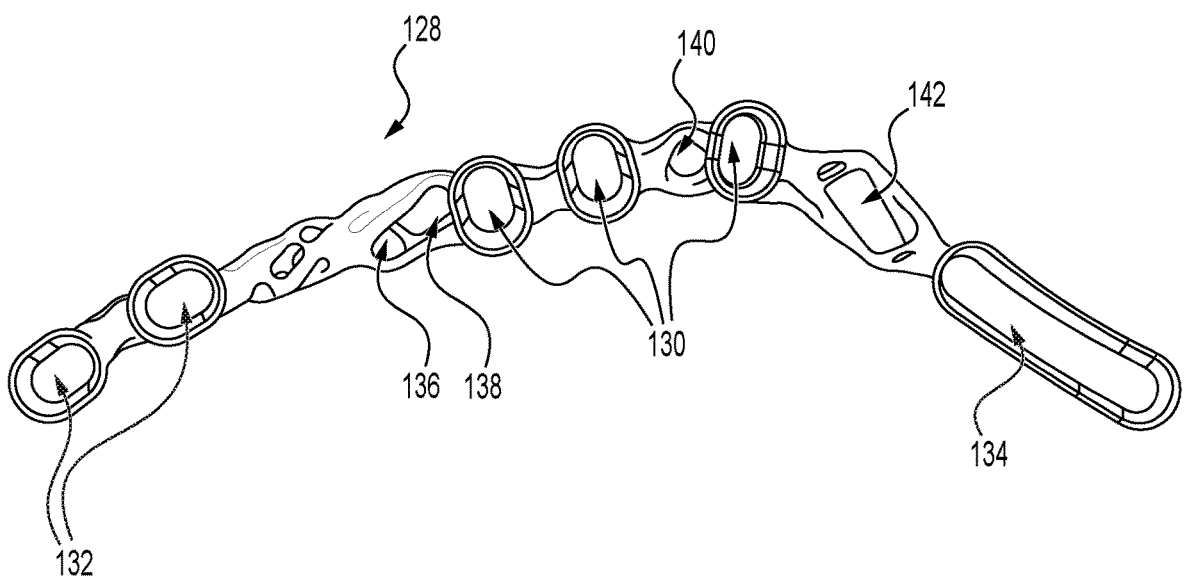
FIG. 16 is a perspective view of a patient-specific plate bridge with a wide variety of geometric shapes forming the slots to custom conform to particular patients and associated medical conditions.

Referring now to FIGS. 15 and 16, a wide variety of plates 104 is shown as a sixth embodiment that can be interconnected in separate units or form one long continuous plate in different shapes and sizes and is generally indicated by the numeral 124 and placed along a human spine 126. This custom plate 128 can be specifically designed to achieve the planned correction, match the desired stiffness to achieve correction and load share with bony elements, and be contoured to match patient anatomy. The orientation of the openings or slots in the custom plate 128 may be adjusted for varying trajectory of the bone screws 102 with preferably, but not necessarily, extended reduction posts 122. In addition, the direction and length of the openings or slots may be adjusted for varying amounts of compression, distraction, derotation, and lateral translation.

The slots 130 at the most rotated vertebrae are rotated in a similar direction to accommodate the inward angle of the bone screws 102 compared to the bone screws 102 with less rotation, such as utilized in slots 132 and 134. The slots or openings are offset to bony anatomy so that the hemispherical nuts 108 may be threaded to reduce the human spine 126 to the custom plate 128. First and second slots, which extend along the spine, 132 and 134, respectively, permit translation of the bone screws 102 and hemispherical nuts 108 along the slots 132 and 134 for compression and distraction. These first slots 132 may accept one bone screw 102, and the second slot 134 may accept multiple bone screws 102 with associated hemispherical nuts 108. Slots 130 in the most rotated part of the human spine 126 permit translation along this slot 130 for lateral translation and derotation. A myriad of types of slots, shown in FIG. 16, can include a small round/rectangular opening 136, a larger oval but almost circular opening 138, a smaller square opening 140, and a larger rectangular opening 142.

The structural portions of the custom plate 128 bridge the slots 130, 132, and 134 such that there is sufficient strength and stiffness for correction and physiological loading, do not interfere with bony anatomy, and minimize the implant profile.

The custom plate 128 can be of a wide variety of shapes and structures that do not interfere with bony anatomy and minimize the implant profile. In addition, the structural portion of the custom plate 128 can be created through generative modeling to optimize stiffness.

Figure 17:
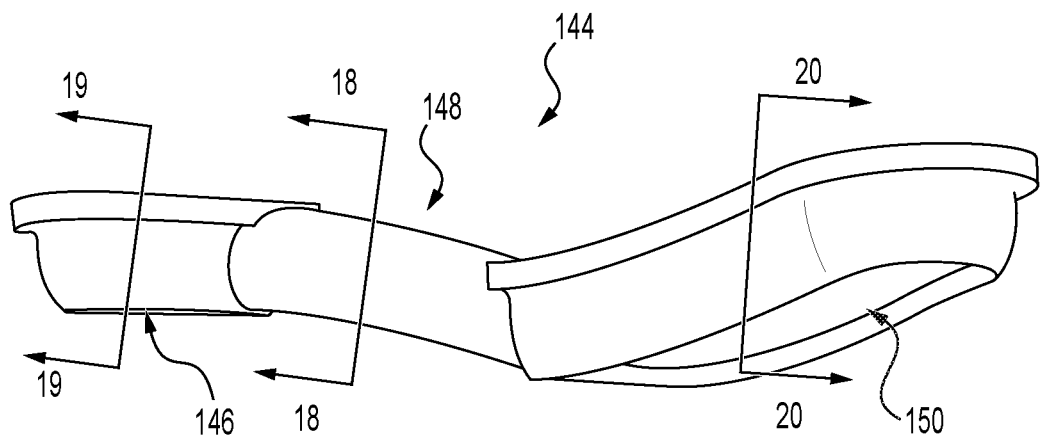
FIG. 17 is a perspective view of a plate bridge with circular and oval slots with a circular connecting member.
Figure 18:
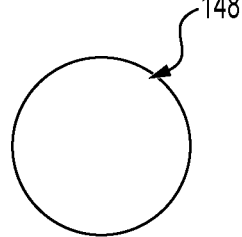
FIG. 18 is a sectional view along line 18-18 in FIG. 17 of the cross-section of the circular member for the plate bridge.
Figure 19:
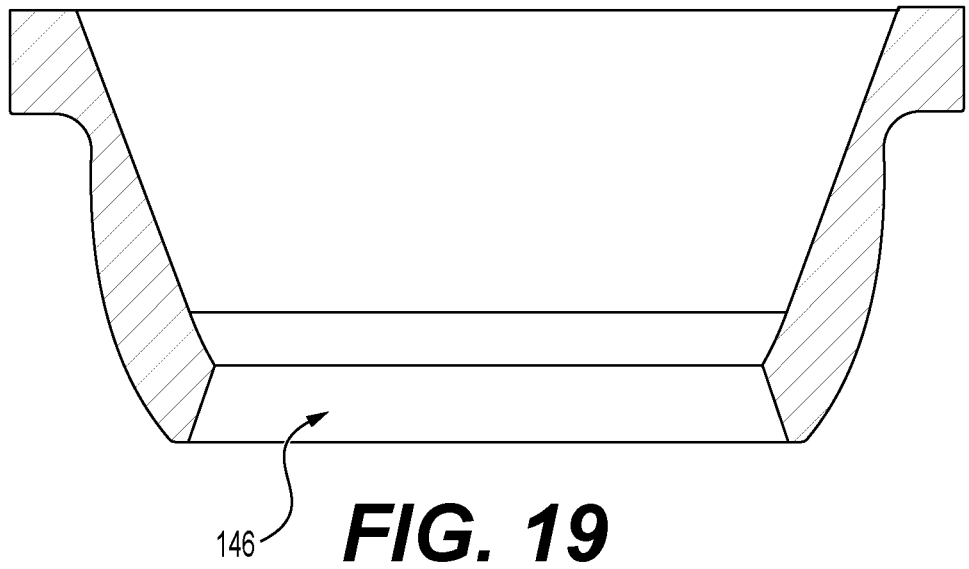
FIG. 19 is a sectional view along line 19-19 in FIG. 17 of the side walls of the circular slot section of the plate bridge.
Figure 20:
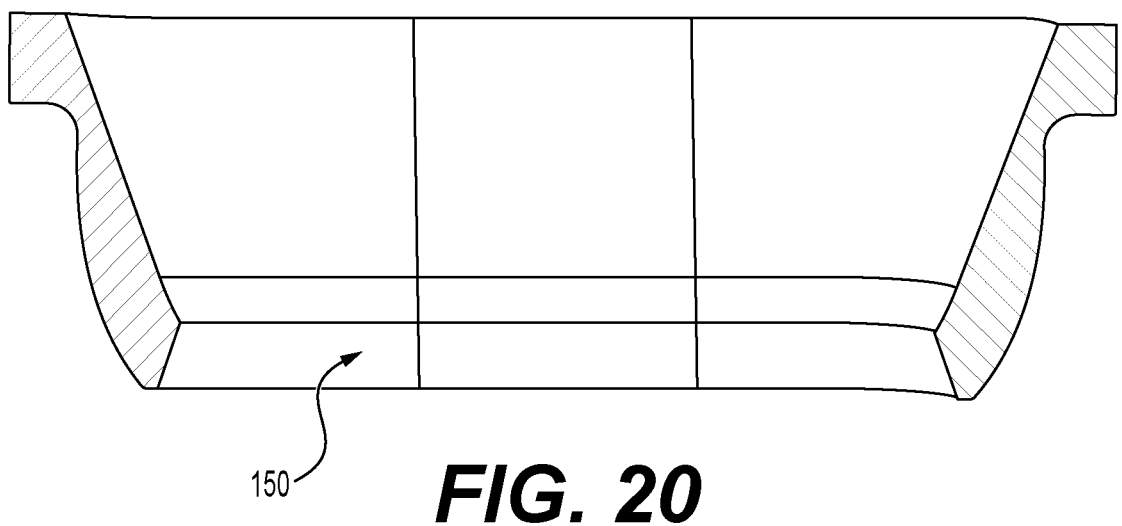
FIG. 20 is a sectional view along line 20-20 in FIG. 17 of the side walls of the oval slot section of the plate bridge.

For example, a variation of a custom plate with a circular cross structure is identified by the numeral 144 in FIG. 17. This includes a circular walled opening 146 and an oval walled opening 150 connected by a circular connecting rod 148. The cross-section of the circular connecting rod 148 is shown in FIG. 18. A cross-section of the circular walled opening 146 is shown in FIG. 19, and a cross-section of the oval walled opening 150 is shown in FIG. 20.

Figure 21:
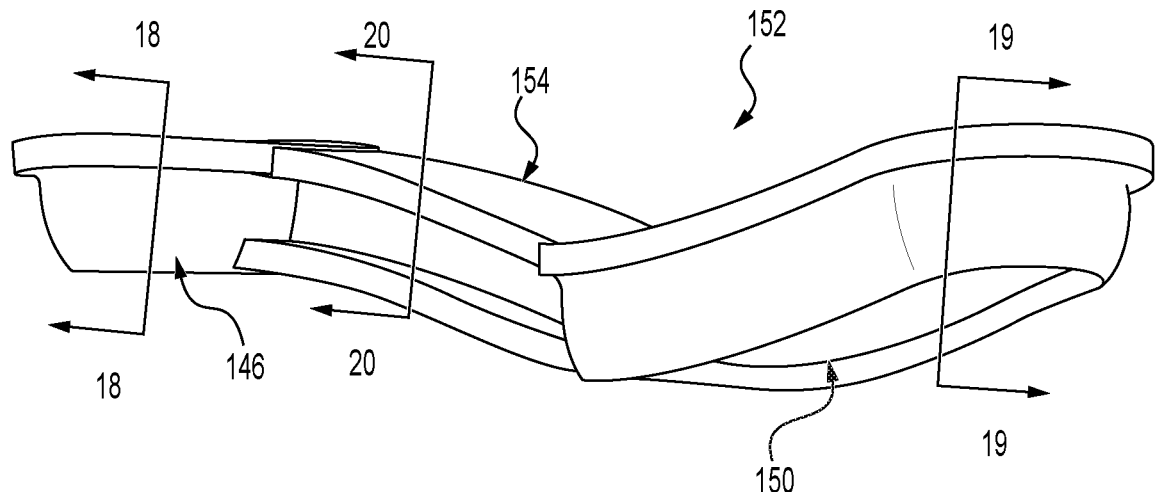
FIG. 21 is a perspective view of a plate bridge with circular and oval slots shown in FIG. 17 and having a connecting member with an I-beam cross-section.
Figure 22:
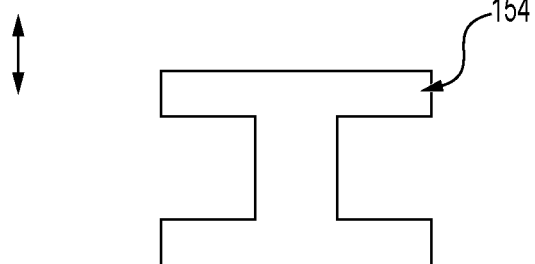
FIG. 22 is a sectional view along line 20-20 in FIG. 21 of the I-beam cross-section of the connecting member.

Another variation is a custom plate with an I-beam cross structure is identified by the numeral 152 in FIG. 21. This includes the same circular walled opening 146 and an oval walled opening 150 referenced above but is now connected by an I-beam connector 154. As the cross-section of the I-beam connector 154 is shown in FIG. 22. These cross-sections' sizes or dimensions may vary to achieve varying stiffnesses and strengths.

There are a number of screwdrivers, instruments, drivers, and screw extender instruments that can be used with the present invention, with additional elements for use with navigated and/or robotic techniques (preferably with screw extender instruments). In navigated and/or robot-assisted surgical procedures, one or more instruments may be tracked using a reference element, array, dynamic reference array, or other suitable tracking device or method. The tracking and/or robotic system may include one or more tracking markers, which are attached or attachable to the instrument and allow the system to detect and localize the instrument's position in three-dimensional (3D) space. A computer platform in combination with a camera tracking system or another 3D localization system may be utilized to track in real-time: the position, rotational orientation, relative location, and movement of the instrument throughout the surgical procedure. Examples of surgical robotic and/or navigation systems can be found, for example, in U.S. Pat. Nos. 10,675,094 and 9,782,229, which are incorporated by reference herein in their entireties for all purposes.

Figure 23:
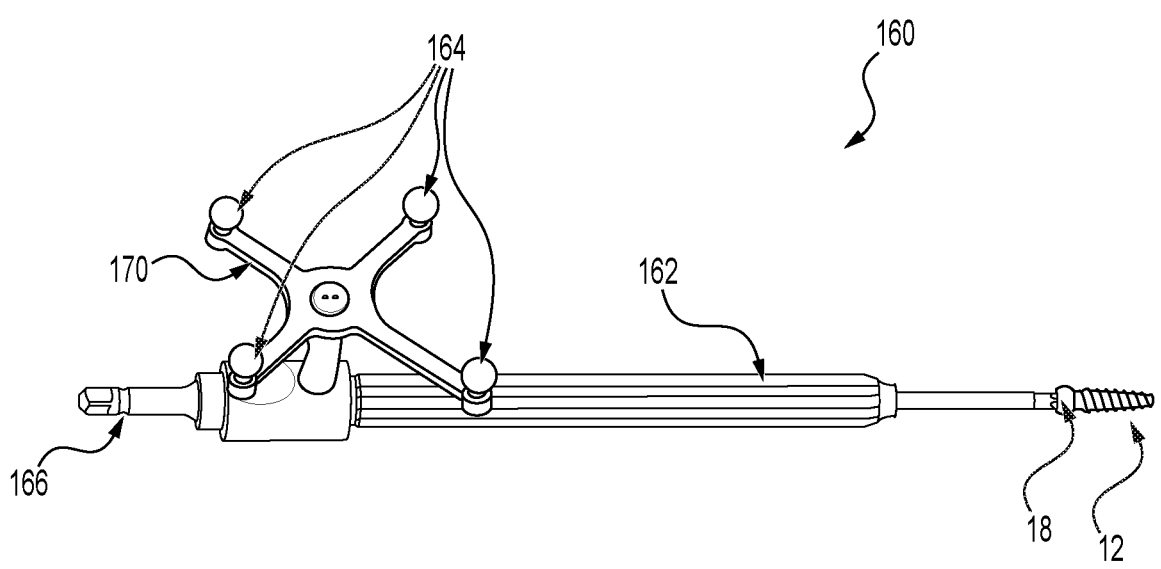
FIG. 23 is a perspective view of navigated robotic screwdriver associated with the first embodiment of the present invention.

In FIG. 23, the navigated driving mechanism 160 includes a navigation feature, such as a tracking array 170, according to one embodiment. The tracking array 170 may secure a plurality of tracking markers 164, such as passive or active markers, in a given configuration. The tracking markers 164 may include optical spherical passive markers, for example. Alternatively, an array of discs may be used to navigate a first screwdriver instrument 166. The tracking array 170 may be axially constrained or attached to the first screwdriver instrument 166 and used to locate the axis and location of the top 18 of bone screw 12 for navigated placement of bone screws 12. This is placed within the aforementioned head fixation assembly 16, which has an attached lateral plate 14. The tracking array 170 is typically, but not necessarily, attachable to the first screwdriver instrument 166.

The navigated driving mechanism 160 includes a first screwdriver instrument 166 and may have an outer body portion 162 with an outer diameter sized and configured to mate with a guide tube of a robotic system. The outer body portion 162 of the first screwdriver instrument 166 may be integral or may mate with an instrument with the desired outer diameter configured to match the end effector guide tube of a robot. When the outer body 162 of the first screwdriver instrument 166 is received through the guide tube of a robot, the robot further allows for the guidance of the screw 12 along a prescribed trajectory.

Figure 24:
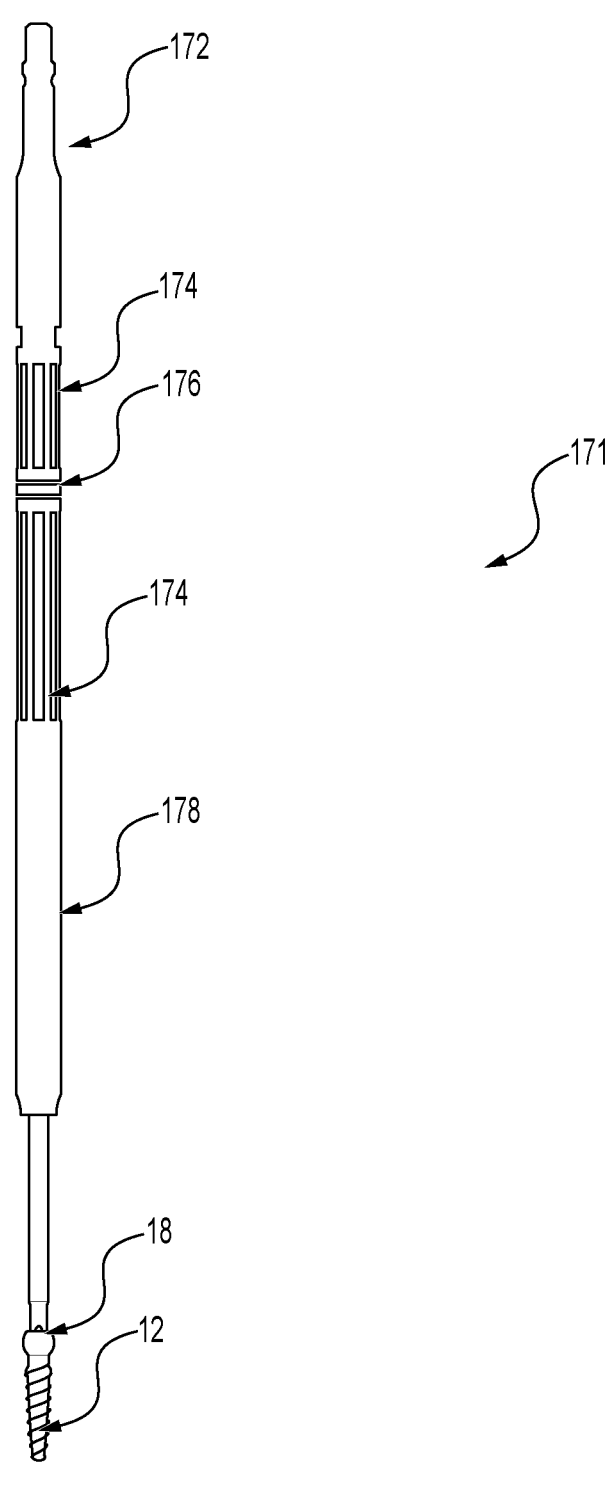
FIG. 24 is a perspective view of a navigation machine vision driving system of the present invention.

In FIG. 24, the navigation machine vision driving system 171 uses the geometry of a second screwdriver instrument 172 to provide navigation. A machine learning algorithm may be used to recognize a known instrument's geometry and/or appearance and track the second screwdriver instrument 172 with visible light. One or more machine vision targets 174 and 176 on the body of the second screwdriver instrument 172 may aid in instrument recognition and tracking by a navigation and/or robotic system. The machine vision targets may include longitudinal, circumferential, or other suitable targets that are marked, coated, or cut directly on the body of the second screwdriver instrument 172. For example, longitudinal targets 174 aid in tracking the orientation and rotation of the instrument, while circumferential targets 176 aid in tracking the distance to the tip of the second screwdriver instrument 172. Unique patterns, spacings, sizes, and shapes of these targets 174, 176 can allow the navigation and/or robotic system to differentiate between otherwise visually similar instruments. In addition, one or more areas of the screw extender instrument 176 may include non-reflective coatings and surface treatments 178 to reduce the effect of reflections or glare from bright operative lights.

Similarly, machine vision targets 174 and 176 may also be used to track the second screwdriver instrument 172 after the bone screws 12 have been placed in the vertebral patient bodies. The head fixation assembly 18, having an attached lateral plate 14, is inserted after placement of the bone screw 12.

Figure 25:
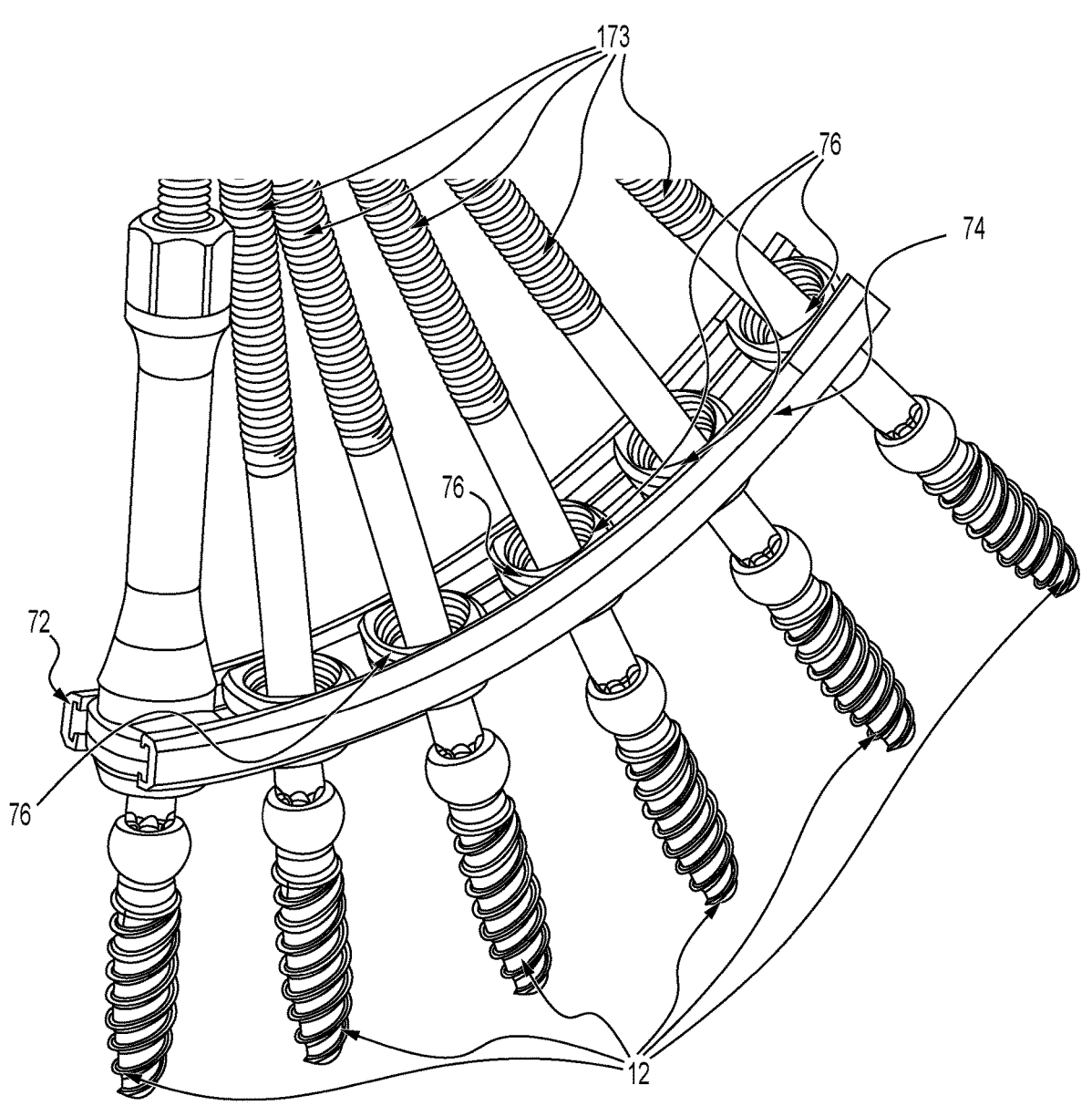
FIG. 25 is a perspective view of a series of screw extenders and pushers used to reduce the series of screws to the head fixation assemblies in accordance with the third embodiment in FIG. 9.

Referring to FIG. 25, there are several second screw extenders 173 that are used to apply to numerous bone screws 12 shown in FIG. 9, which is the second embodiment having a series of bone screws 12 held in a series of head fixation assemblies 76. and including both a first lateral plate 72 and a second lateral plate 74.

The navigated screw extender instruments 173 described above allow for the accurate placement of the screw 12 in a pre-planned location, along with a recording of the final position of screw 12 for use with subsequent vertebral body tracking. In addition, the varying methods for tracking instruments, including the screw extenders, allow for varying slimness and complexity of marker and navigated feature design, the robustness of tracking, robustness of differentiation between simultaneously tracked instruments, computational resources required, and/or detection of loss of navigation integrity.

A screw extender instrument may be secured to the top of the bone screw 18 by one of several different mechanisms. In one embodiment, the screw extender instrument includes one or more ball bearings receivable in the drive and engagement recess of the top of the bone screw 18, thereby allowing for a rigid connection between the screw extender instrument and the screw head. The drive and engagement recess in the screw head may include a recessed drive portion configured to interface with the outer sleeve and one or more recessed engagement portions configured to interface with one or more ball bearings of the screw extender instrument. The engagement portions may each define an undercut with a circular cross-section sized and dimensioned to interface with the complimentary size and shape ball bearing. The screw extender instrument may include a helical ramp at a distal end of the inner shaft, and when the inner shaft is rotated and/or translated, the ball bearing is seated into the engagement portion of the screw head. The screw extender instrument may include a pair of ball bearings, and the inner shaft may include a pointed tip that, when translated downwardly, forces the ball bearings outwardly into the engagement portions of the top of the bone screw 18. In another embodiment, the screw extender instrument includes a threaded portion along an outer portion of the outer sleeve, which secures the instrument to the top of the bone screw 18. In another embodiment, the screw extender instrument includes a prong extending from the outer sleeve configured to wedge between the screw head and the inner shaft. In yet another embodiment, the screw extender instrument includes one or more flexible portions separated by one or more slits, and the flexible portions can be expanded when the inner shaft is translated toward the top of the bone screw 18, thereby securing the instrument to the top of the bone screw 18. Therefore, numerous permutations of screw extender instruments are known in the art. These examples are described in U.S. Published Patent Application No. 2023/0010173 A1, published Jan. 12, 2023.

Figure 26:
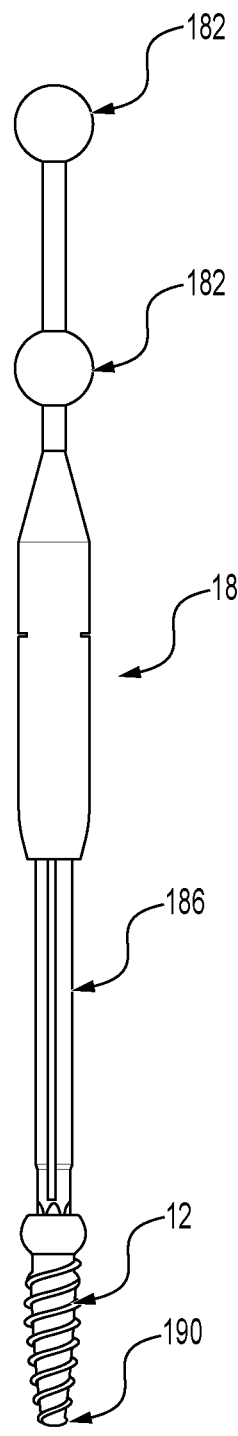
FIG. 26 is a perspective view of a navigated robotic screwdriver with a two marker array.

Referring to FIG. 26, another navigated robotic screwdriver is indicated by the numeral 180 and includes a two marker array with fiducial markers 182, preferably attachable, for navigated and/or robotic screw placement. For example, a pair of fiducial markers 182 may be attached to the navigated robotic screwdriver 180 or directly to some other type of array. The fiducial markers 182 may be passive spherical markers or discs, as illustrative, but nonlimiting, examples. An array of two or more fiducial markers 182 may be aligned with the central axis 186 of the navigated robotic screwdriver 180 and bone screw 12. Attaching an array with two or more fiducial markers 182 aligned with the central axis 186 of the bone screw 12 at a known distance from the tip 190 of the bone screw 12 allows tracking of the orientation of the central axis 186 of the bone screw 12 and the location of its tip 190, but not its rotation.

Figure 27:
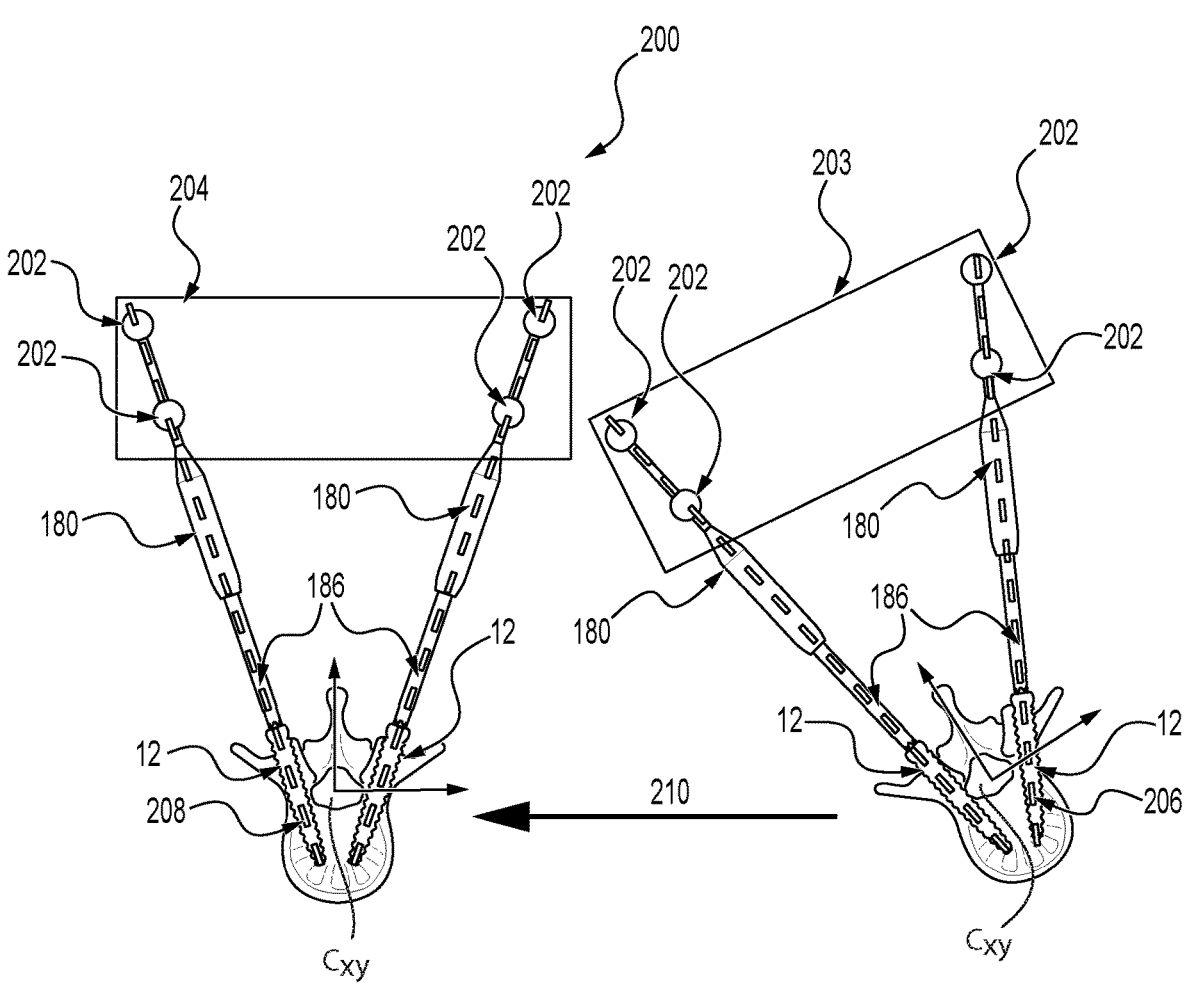
FIG. 27 is a perspective view of vertebral body tracking with screw extender instruments and four fiducial markers.

Referring now to FIG. 27, a bone tracking system 200 with four fiducial markers 202 is shown. The first and second pedicle bone screws 12 are inserted into the bone at an initial position 206 in space. Once the screws 12 have been placed, the navigated robotic screwdriver 180 continues to track the location and orientation of the vertebral body, sacrum, and/or pelvis using the location and orientation of the placed bone screws 12. A transformation 210 of the location and/or orientation of the bone in space due to translation and/or rotation results in a subsequent position 208 identified by the bone tracking system 200. The navigated robotic screwdriver 180 thereby allows for continued tracking of the bone. Although FIG. 27 is described with respect to navigated robotic screwdriver 180, it will be appreciated that the tracking methods may apply to any of the screw extender instruments or other navigatable instruments or drivers described herein.

According to one illustrative, but nonlimiting, embodiment, a system and method for individual extender array tracking may include one or more of the following steps: (1) the orientation of the central axes 186 of the bone screws 12 are recorded at the completion of navigated insertion of bone screws 12 into the vertebral body at initial position 206; (2) navigated robotic screwdrivers 180 are recorded by the motion tracking system 200 during manipulation of the spine; (3) the vectors defining the central axes 186 of the navigated robotic screwdrivers 180 are calculated (for discs or markers 202 placed along the central axes 186, this is the difference in coordinates between the discs or markers 202 and if, at any time, the relative orientation of these vectors becomes significantly different than the vectors of the placed bone screws 12 then navigation integrity has been lost and the system will stop tracking); (4) these two vectors are compared against the original orientation of the central axes 186 of the bone screws 12 to define the transformation matrix that corresponds to the rigid body translation and rotation of the vertebral body; and (5) a transformation matrix is applied to the initial position 206 of the vertebral body coordinate system to update its translation and rotation in space to the subsequent position 208.

According to another embodiment, a system and method for combined extender array tracking may include one or more of the following steps: (1) the orientation and position of the central axes 186 of the bone screws 12 are recorded at the completion of navigated insertion of bone screws 12 into the vertebral body; (2) locations of the fiducial markers

202 and/or navigated robotic screwdrivers 180 are modeled by calculating their distance along the central axes 186 of the navigated robotic screwdrivers 180; (3) these locations define a first array 203 or combined instrument model to be tracked and recognized by the vision aspects of this bone tracking system 200 (if the navigated robotic screwdrivers 180 move significantly with respect to each other, a different second array 204 or combined instrument model cannot be recognized and the system will stop tracking); (4) These arrays 203, 204 or combined instrument models are recorded by the motion tracking system during manipulation of the patient spine; (5) the coordinate system of the arrays 203, 204, respectively, or combined screw extender instrument models are compared against their modeled original or initial coordinate systems position 206 to define a transformation matrix that corresponds to the rigid body translation and rotation of the patient vertebral body; and (6) a transformation matrix is applied to the patient vertebral body coordinate system to update its translation and rotation in space to subsequent position 208.

The transformation matrix is shown below in Equation (1):

$$x_j = T_{ij}X_i \rightarrow \begin{bmatrix} x \\ y \\ z \\ 1 \end{bmatrix} = \begin{bmatrix} r_{xx} & r_{xy} & r_{xz} & t_x \\ r_{yx} & r_{yy} & r_{yz} & t_y \\ r_{zx} & r_{zy} & r_{zz} & t_z \\ 0 & 0 & 0 & 1 \end{bmatrix} \begin{bmatrix} X \\ Y \\ Z \\ 1 \end{bmatrix} \qquad \text{Equation 1}$$

With twenty-six individual vertebrae, the sacrum, and the pelvis, many arrays and objects may need to be simultaneously recognized and tracked. There are multiple methods that may be used to allow recognition of the screw extender instruments, including instruments, extenders, drivers, and so forth, and the vertebral body that is being tracked. Just four of these methods are described below.

A first method is a position cross-reference: This is where the position of the tip of the navigated robotic screwdriver 180 is calculated and ordered according to its height along the patient's central axis. Vertebral patient bodies may be ordered superior to inferior and do not exchange locations during surgical intervention. Positions closer to the right of the patient coordinate system or the right of the vertebral body coordinate system can be identified as the right pedicle bone screw or left pedicle bone screw conversely.

A second method is a unique fiducial array. This unique array of fiducial markers or discs could be recognized by their unique distances between markers.

A third method is unique machine vision targets: A unique pattern, size, or color of machine vision targets may be used to differentiate each screw extender instrument.

A fourth method is a unique combined extender array: By utilizing the method for combined extender array tracking described above, the unique trajectory and position of the bone screws 12 create a unique array pattern that can be recognized by their unique distances between markers 202.

Once patient vertebral bodies are tracked, changes in position and orientation can be used to provide feedback to the user, such as displaying the current position and orientation of vertebral bodies, calculating spinal alignment parameters such as lordosis and kyphosis, and/or calculating for aminal height and estimated tension/compression placed on neural elements from the displacements of tracked adjacent vertebral bodies.

Tracking of patient vertebral bodies allows for real-time intraoperative feedback to be provided to the user on measures that typically require discrete X-ray images to be taken. Spinal alignment, neural decompression, and other clinically relevant parameters can be assessed continuously for the user to adapt their intraoperative intervention to achieve desired surgical goals. In addition, anatomy can be visualized more accurately by displaying the locations of bony anatomy in their current locations instead of relying on a radiograph that does not reflect surgical changes.

Figure 28:
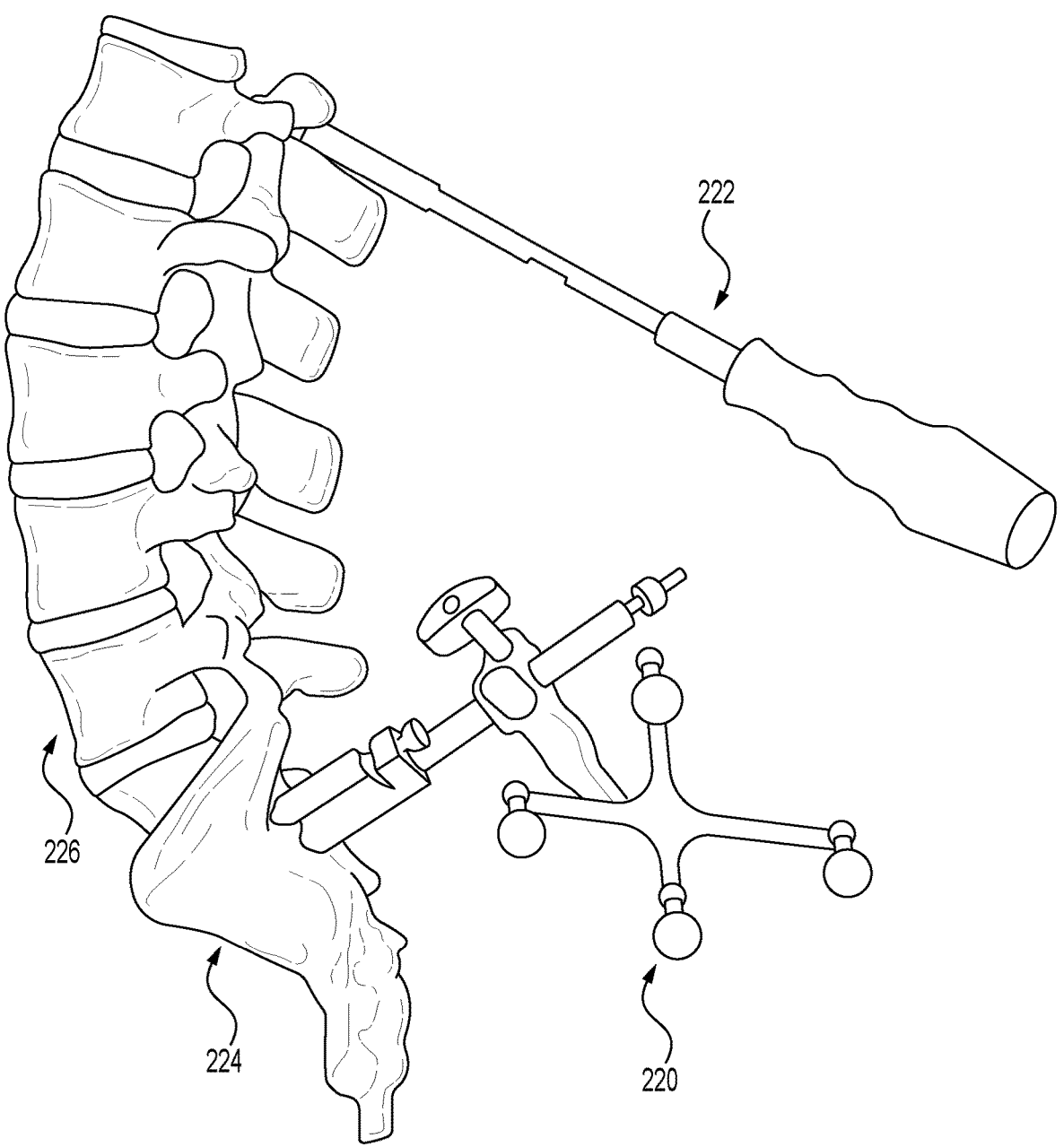
FIG. 28 is a perspective view of a traditional Dynamic Reference Base (DRB) that is placed on the sacrum below the lumbar spine.
Figure 29:
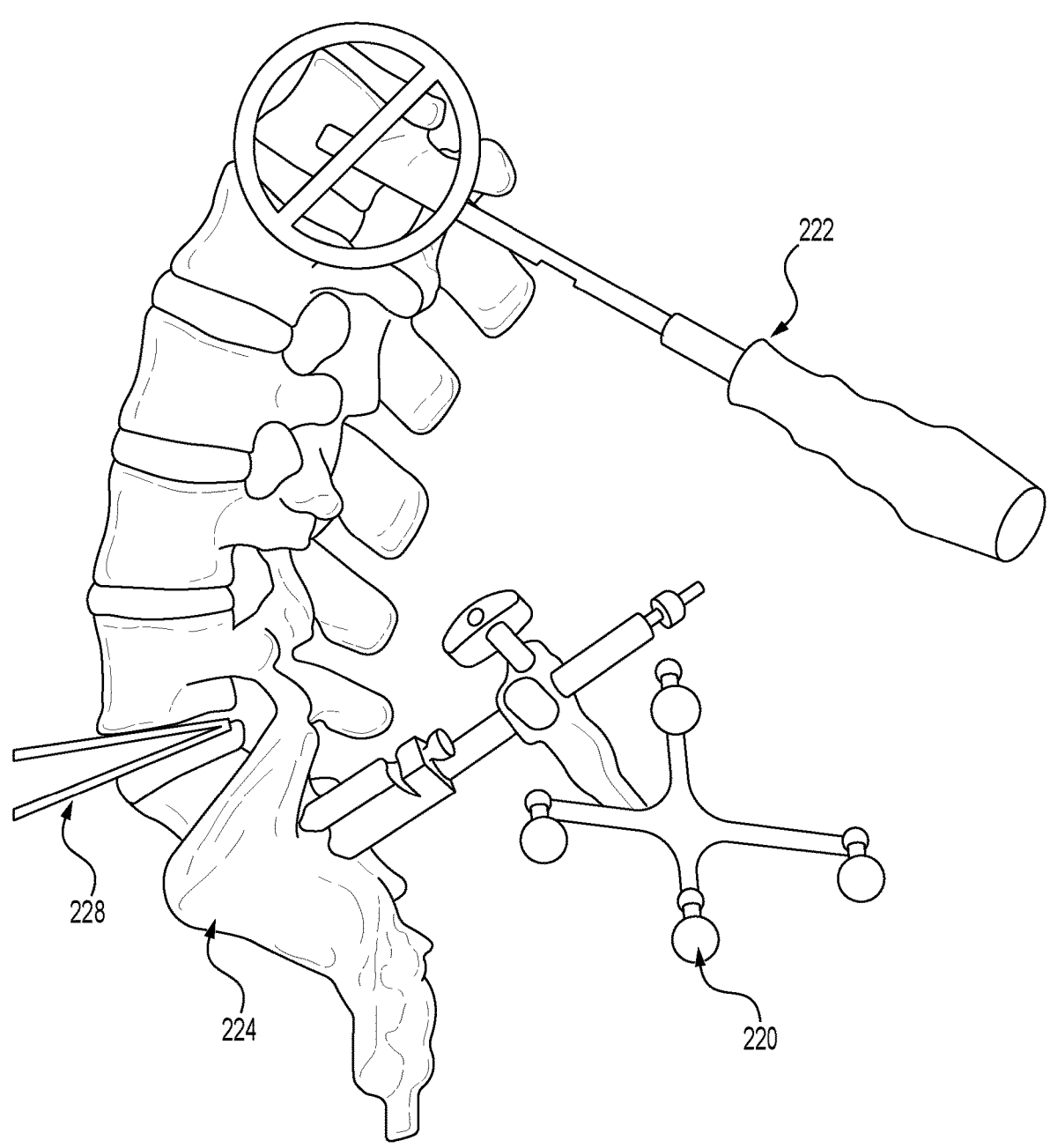
FIG. 29 is also a perspective view of a traditional Dynamic Reference Base (DRB) when lordosis is added between L5 and S1, showing that although the DRB's location does not physically change, it is being incorrectly tracked and there is a discrepancy between the DRB's actual location (in the middle of the vertebral body) versus where the system is displaying the location of the tool on the posterior elements, as shown in FIG. 28.
Figure 30:
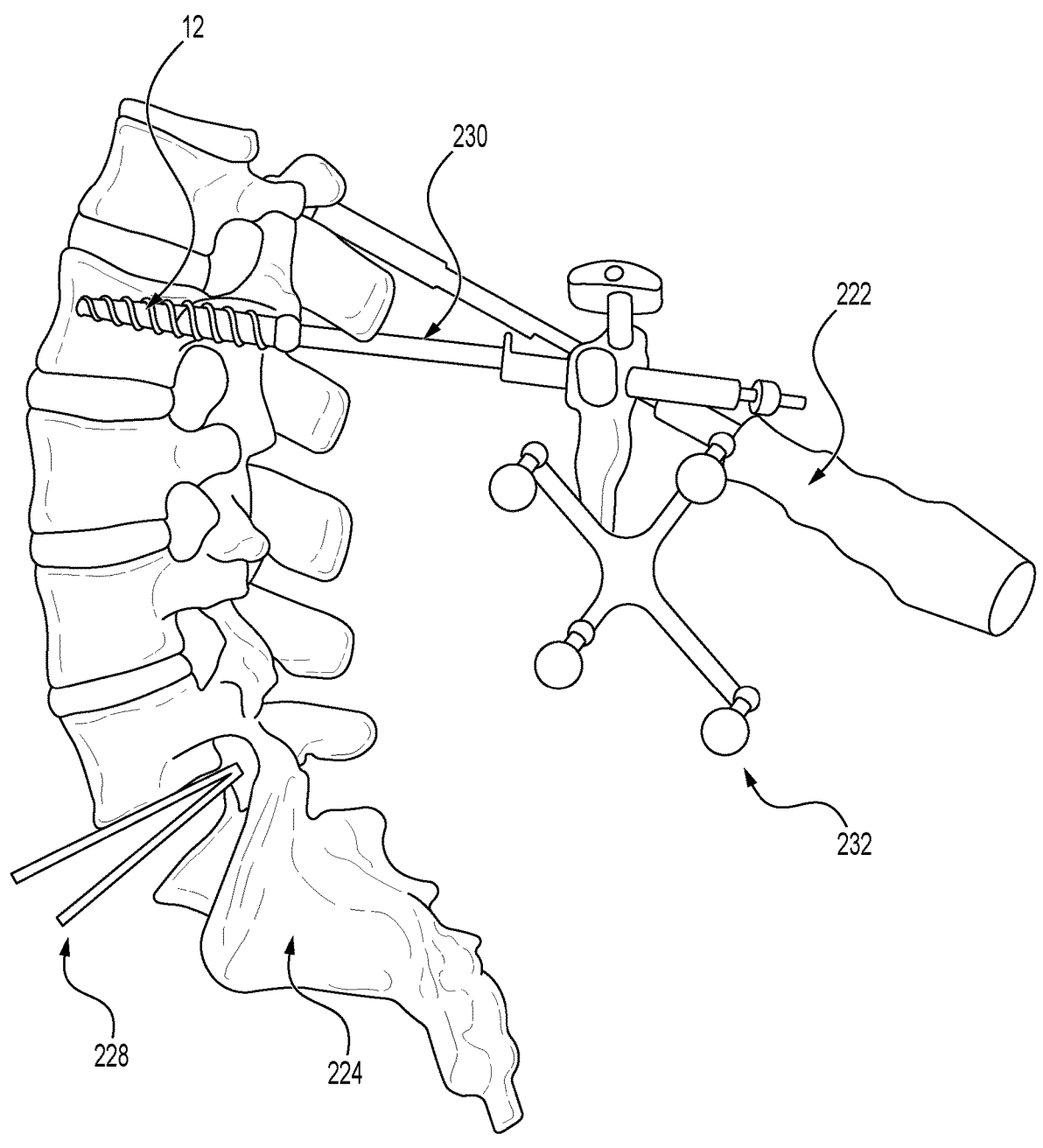
FIG. 30 is where a traditional Dynamic Reference Base (DRB) is replaced with an implanted bone screw and navigable screw extender instrument, where an array of the navigable screw extender acts as the local Dynamic Reference Base (DRB) to locate imaging.
Figure 31:
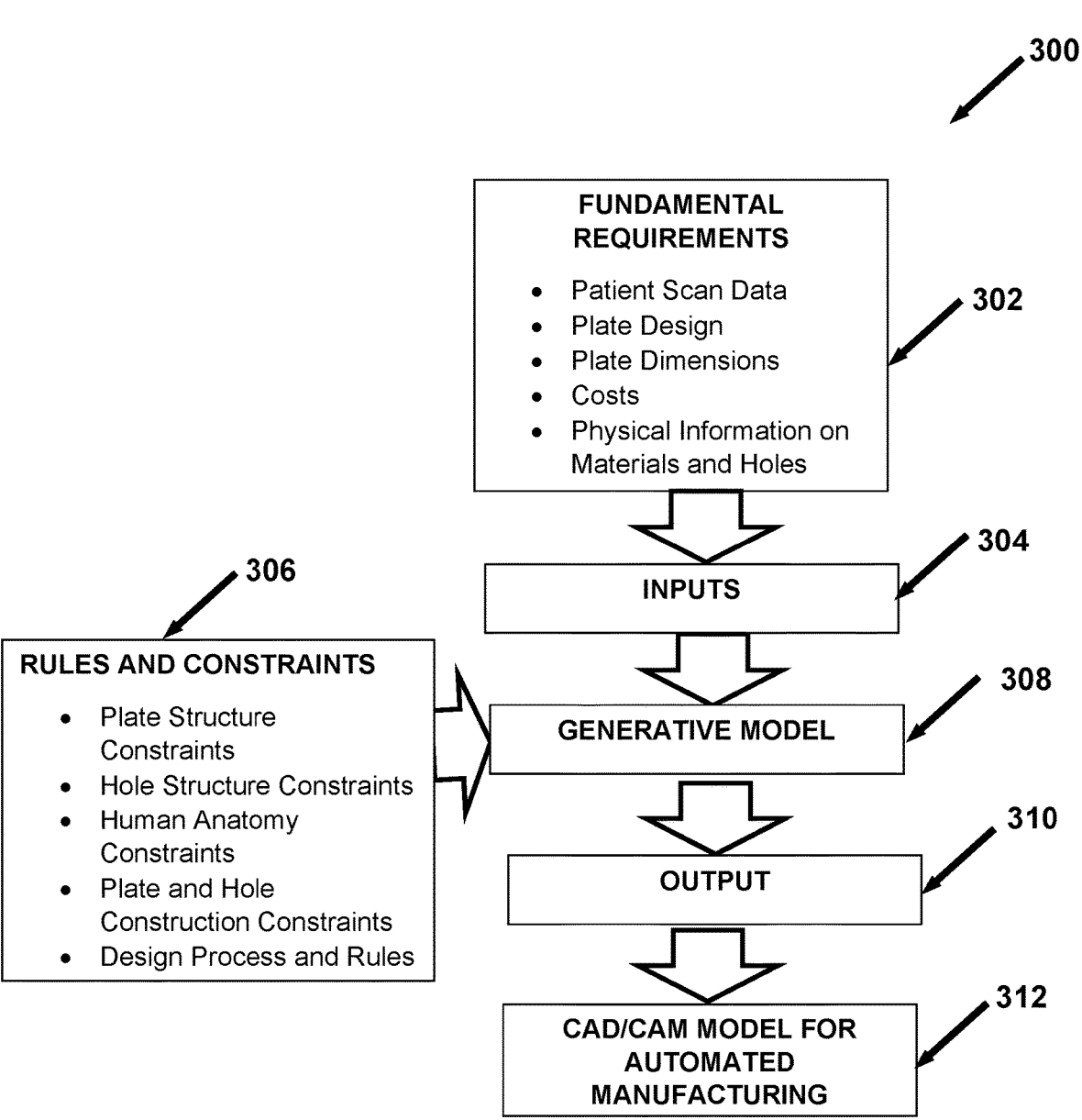
FIG. 31 is a flowchart for the generative model creation of a plate bridge.

Referring now to FIGS. 28, 29, and 30, and initially FIG. 30, navigation integrity may be improved by using a placed bone screw 12 and a screw extender instrument 230 as a local Dynamic Reference Base (DRB) instead of a traditional Dynamic Reference Base (DRB) anchored further from the vertebral body being manipulated. The Dynamic Reference Base (DRB) is used to locate imaging to patient anatomy, and if patient anatomy displaces outside of rigid body motion, then navigation integrity is affected. When the Dynamic Reference Base (DRB) is instead attached closer to an area of interest, the navigation integrity error can be reduced.

Referring now to FIG. 28, which shows the traditional placement of the Dynamic Reference Base (DRB) 220 on the spine. For example, a traditional Dynamic Reference Base (DRB) 220 may be placed on the sacrum 224 below the lumbar spine 226. The screw extender 222 may be placed on the posterior elements of L1 or other vertebrae. As shown in FIG. 29, when lordosis 228 is added between L5 and S1, the sacrum 224 stays at the same place with respect to the Dynamic Reference Base (DRB) 220, but the location of the screw extender 222 changes and is now located in the middle of the vertebral body. The navigation system would erroneously show the position of the screw extender 222 on the posterior elements, thereby resulting in an inaccuracy in navigation.

In FIG. 30, the traditional Dynamic Reference Base (DRB) 220 is replaced with the implanted bone screw 12 and screw extender instrument 230. Although a screw extender instrument 230 is shown, it will be appreciated that any of the navigatable screw extender instruments may be substituted. The tracking array 232 of the screw extender instrument 230 acts as the local Dynamic Reference Base (DRB) to locate imaging. The bone screw 12 and screw extender instrument 230 and resulting tracking are now located in close proximity to the screw extender 222. In this configuration, a change in lordosis 228 does not result in a change of the apparent tool location. Thus, the navigation system properly shows the position of the screw extender 222 on the posterior elements, thereby resulting in accurate navigation. In other words, the use of the screw extender instrument 230 as a local Dynamic Reference Base (DRB) allows for the positioning of Dynamic Reference Base (DRB)s in additional bony anatomy closer to areas of interest to reduce errors in navigation integrity caused by the non-rigid motion of the spine. This allows navigation integrity to be maintained more readily in longer constructs across many flexible portions of the spine or in interventions where the spine is flexible, for example, in pediatric deformity or when significant osteotomies are performed.

From the foregoing, it can be seen that the present disclosure accomplishes at least all of the stated objectives.

LIST OF REFERENCE CHARACTERS

The following table of reference characters and descriptors are not exhaustive, nor limiting, and include reasonable equivalents. If possible, elements identified by a reference character below and/or those elements which are near ubiquitous within the art can replace or supplement any element identified by another reference character.

TABLE 1

List of Reference Characters

| | |
|---|---|
| 2 | Prior art head fixation assembly |
| 3 | Prior art rod, e.g., interconnecting member |
| 4 | Prior art top locking mechanism |
| 5 | Height of prior art head fixation assembly |
| 10 | Pedicle screw assembly |
| 12 | Bone screw |
| 14 | Lateral interconnecting member, e.g., lateral plate |
| 16 | Head fixation assembly |
| 18 | Top of the bone screw |
| 19 | Recess |
| 20 | Lower body |
| 22 | Upper body |
| 24 | Locking bolt |
| 26 | Modular clip |
| 28 | Downward extending prong |
| 30 | Upward extending prong |
| 32 | Upward-facing lower groove of lateral plate |
| 34 | Downward-facing upper groove of the lateral plate |
| 36 | Upper flange of locking bolt |
| 38 | Threaded opening in lower body |
| 46 | Vertical offset |
| 48 | Implant |
| 52 | Lamina |
| 54 | Transverse process |
| 56 | Spinous process |
| 58 | Run-on-rod |
| 60 | Second embodiment |
| 62 | Interconnecting member, e.g., c-shaped |
| 63 | Cylindrical opening |
| 64 | Upper half circle dovetail prong |
| 66 | Lower half circle dovetail prong |
| 70 | Third embodiment |
| 72 | First lateral plate - interconnecting member |
| 74 | Second lateral plate- interconnecting member |
| 76 | Head fixation assembly |
| 78 | Center locking screw |
| 80 | Upper member |
| 82 | Upward-facing upper groove in the upper member |
| 84 | Lower member |
| 86 | Downward-facing lower groove in the lower member |
| 88 | Threaded opening |
| 90 | Upward facing lower prong of the first lateral plate |
| 92 | Downward extending prong of the first lateral plate |
| 94 | Upward facing lower prong of the second lateral plate |
| 96 | Downward extending prong of the second lateral plate |
| 100 | Fourth embodiment |
| 102 | Bone screw |
| 104 | Plate |
| 106 | Curved surface of the bone screw |
| 108 | Hemispherical nut |
| 110 | Pivoting washer |
| 112 | Mating cephalad-caudal curved surface of the pivotal washer |
| 114 | Medial-lateral curved surface of the pivoting washer |
| 116 | Exterior curved surface of the plate |
| 118 | Inside slot |
| 120 | Fifth embodiment |
| 122 | Bone screws with extended reduction posts |
| 124 | Sixth embodiment of interconnected plate units or a long continuous plate |
| 126 | Human spine |
| 128 | Custom plate |
| 130 | Slots in the most rotated vertebrae |
| 132 | First slot with less rotation that extends along the spine |
| 134 | Second slot with less rotation that extends along the spine |
| 136 | Small round/rectangular opening |
| 138 | Larger oval but almost circular opening |
| 140 | Smaller square opening |
| 142 | Larger rectangular opening |
| 144 | First custom plate with a circular cross structure |
| 146 | Circular walled opening |
| 148 | Circular connecting rod |
| 150 | Oval walled opening |
| 152 | A second custom plate with an I-beam cross structure |
| 154 | I-beam connector |

TABLE 1-continued

List of Reference Characters

| | |
|---|---|
| 160 | Navigated driving mechanism |
| 162 | Outer body portion |
| 164 | Tracking markers |
| 166 | First screwdriver instrument |
| 170 | Tracking array |
| 171 | Navigation machine vision driving system |
| 172 | Second screwdriver instrument |
| 173 | Screw extender |
| 174 | Longitudinal machine vision target |
| 176 | Circumferential machine vision target |
| 178 | Non-reflective coatings and surface treatments |
| 180 | Navigated robotic screwdriver |
| 182 | Fiducial markers |
| 186 | Central axes |
| 190 | Tip of a bone screw |
| 200 | Bone tracking system |
| 202 | Fiducial markers (or discs) |
| 203 | First array |
| 204 | Second array |
| 206 | Initial position |
| 208 | Subsequent position |
| 210 | Transformation |
| 220 | Traditional DRB |
| 222 | Screw extender |
| 224 | Sacrum |
| 226 | Lumbar spine |
| 228 | Lordosis |
| 230 | Screw extender instrument |
| 232 | Tracking array operating as local DRB |
| 300 | Generative model creation of a plate bridge flowchart |
| <302> | Obtain fundamental requirements |
| <304> | Inputs |
| <306> | Utilize rules and constraints |
| <308> | Generative model |
| <310> | Output |
| <312> | CAD/CAM model |

Glossary

Unless defined otherwise, all technical and scientific terms used above have the same meaning as commonly understood by one of ordinary skill in the art to which embodiments of the present disclosure pertain.

The terms "a," "an," and "the" include both singular and plural referents.

The term "or" is synonymous with "and/or" and means any one member or combination of members of a particular list.

As used herein, the term "exemplary" refers to an example, an instance, or an illustration, and does not indicate a most preferred embodiment unless otherwise stated.

The term "about" as used herein refers to slight variations in numerical quantities with respect to any quantifiable variable. Inadvertent error can occur, for example, through use of typical measuring techniques or equipment or from differences in the manufacture, source, or purity of components.

The term "substantially" refers to a great or significant extent. "Substantially" can thus refer to a plurality, majority, and/or a supermajority of said quantifiable variables, given proper context.

The term "generally" encompasses both "about" and "substantially."

The term "configured" describes structure capable of performing a task or adopting a particular configuration. The term "configured" can be used interchangeably with other similar phrases, such as constructed, arranged, adapted, manufactured, and the like.

Terms characterizing sequential order, a position, and/or an orientation are not limiting and are only referenced according to the views presented.

The "invention" is not intended to refer to any single embodiment of the particular invention but encompass all possible embodiments as described in the specification and the claims. The "scope" of the present disclosure is defined by the appended claims, along with the full scope of equivalents to which such claims are entitled. The scope of the disclosure is further qualified as including any possible modification to any of the aspects and/or embodiments disclosed herein which would result in other embodiments, combinations, subcombinations, or the like that would be obvious to those skilled in the art.

What is claimed is:

1. A pedicle screw assembly, comprising:
at least one head fixation assembly having an upper body and a lower body with an opening in a bottom portion of the lower body;
at least one bone screw positioned between the upper body and the lower body of the head fixation assembly that extends outward from the opening in the bottom portion of the lower body;
at least one lateral interconnecting member to stabilize at least one bone in a patient, wherein the at least one head fixation assembly is transversely attached to the at least one lateral interconnecting member; and
at least one securing mechanism to lock the upper body to the lower body to prevent polyaxial motion and translation along the at least one interconnecting member, wherein the at least one interconnecting member includes both a first plate and a second plate positioned in parallel on each side of the head fixation assembly with the upper body of the head fixation assembly includes an upward extending prong that interconnects into a downward facing upper groove in the first lateral plate and a downward facing upper groove in the second lateral plate and the lower body of the head fixation assembly includes a downward extending prong that interconnects into an upward facing lower groove in the first lateral plate and an upwardly facing lower groove in the second lateral plate.

2. The pedicle screw assembly according to claim 1, wherein the at least one lateral interconnecting member is a lateral plate.

3. The pedicle screw assembly according to claim 2, wherein the upper body of the head fixation assembly includes an upward extending prong that interconnects into a downward facing upper groove in the lateral plate, and the lower body of the head fixation assembly includes a downward extending prong that interconnects into an upward facing lower groove in the lateral plate.

4. The pedicle screw assembly according to claim 1, further comprising a modular clip that secures the bone screw within the lower body of the head fixation assembly.

5. The pedicle screw assembly according to claim 1, wherein the securing mechanism includes a locking bolt that connects the upper body to the lower body of the head fixation assembly.

6. The pedicle screw assembly according to claim 1, wherein the securing mechanism includes a locking screw that engages the upper body of the head fixation assembly.

7. The pedicle screw assembly according to claim 1, wherein the at least one interconnecting member having a cylindrical opening and the upper body of the head fixation assembly includes an upper half circle dovetail prong that interconnects into the cylindrical opening of the interconnecting member and the lower body of the head fixation assembly includes a lower half circle dovetail prong that interconnects into the cylindrical opening of the interconnecting member and allows angulation of the interconnecting member.

8. The pedicle screw assembly according to claim 7, wherein the interconnecting member is c shaped.

9. A method of installing a pedicle screw assembly, the method comprising:
at least partially inserting the at least one bone screw into a bone of the patient with the at least one screw extender instrument;
attaching a head fixation assembly to the at least one screwdriver instrument and inserting the head fixation assembly over the at least one bone screw;
attaching at least one lateral interconnecting member to the head fixation assembly, wherein the at least one interconnecting member includes both a first plate and a second plate positioned in parallel on each side of the head fixation assembly with the upper body of the head fixation assembly includes an upward extending prong that interconnects into a downward facing upper groove in the first lateral plate and a downward facing upper groove in the second lateral plate and the lower body of the head fixation assembly includes a downward extending prong that interconnects into an upward facing lower groove in the first lateral plate and an upwardly facing lower groove in the second lateral plate;
further reducing the at least one bone screw into the head fixation assembly with the at least one screwdriver instrument; and
connecting a securing mechanism to lock an upper body of the head fixation assembly to the lower body of the head fixation assembly to prevent polyaxial motion and translation along the at least one interconnecting member.

10. The method of installing a pedicle screw assembly according to claim 9, wherein the at least one lateral interconnecting member is a lateral plate, and the upper body of the head fixation assembly includes an upward extending prong that interconnects into a downward-facing upper groove in the lateral plate, and the lower body of the head fixation assembly includes a downward extending prong that interconnects into an upward facing lower groove in the lateral plate.

11. The method of installing a pedicle screw assembly according to claim 9, wherein the at least one interconnecting member includes both a first plate and a second plate positioned in parallel on each side of the head fixation assembly with the upper body of the head fixation assembly includes an upward extending prong that interconnects into a downward facing upper groove in the first lateral plate and a downward facing upper groove in the second lateral plate and the lower body of the head fixation assembly includes a downward extending prong that interconnects into an upward facing lower groove in the first lateral plate and an upwardly facing lower groove in the second lateral plate.

12. The method of installing a pedicle screw assembly according to claim 9, wherein the at least one lateral interconnecting member having a cylindrical opening and the upper body of the head fixation assembly includes an upper half circle dovetail prong that interconnects into the cylindrical opening of the lateral interconnecting member and the lower body of the head fixation assembly includes a lower half circle dovetail prong that interconnects into the cylindrical opening of the lateral interconnecting member and allows angulation of the lateral interconnecting member.

13. The method of installing a pedicle screw assembly according to claim 9, wherein the at least one bone screw that includes both a first bone screw and a second bone screw, and the at least one screw extender instrument that includes both a first navigatable screwdriver instrument and a second navigatable screwdriver instrument, wherein each navigatable screwdriver instrument includes a two marker array with fiducial markers aligned along a central axis of the applicable bone screw for navigated and/or robotic screw placement, wherein once the first and second bone screws have been placed, the first and second screwdriver instruments continue to track the location and orientation of a patient's bone using the location and orientation of the placed first and second bone screws.

14. The method of installing a pedicle screw assembly according to claim 13, wherein at least one of the first and second navigatable screwdriver instruments function as a local dynamic reference base, thereby improving navigation integrity.

15. The method of installing a pedicle screw assembly according to claim 13, the orientation of the central axes of the bone screws and first and second navigatable screwdriver instruments are recorded at an initial position with vectors defining the central axes of the navigatable screw extender instruments are then calculated.

16. The method of installing a pedicle screw assembly according to claim 13, wherein the orientation and position of the central axes of the first and second bone screws are recorded at an initial position with locations of the fiducial markers modeled by calculating their distance along the central axes of the first and second screw extenders defining an array to be tracked and recognized.

* * * * *